US011763918B2

(12) United States Patent
Baluch et al.

(10) Patent No.: US 11,763,918 B2
(45) Date of Patent: Sep. 19, 2023

(54) METHOD AND APPARATUS FOR THE ACCESS TO BIOINFORMATICS DATA STRUCTURED IN ACCESS UNITS

(71) Applicant: GENOMSYS SA, Lausanne (CH)

(72) Inventors: Mohamed Khoso Baluch, Chantilly, VA (US); Claudio Alberti, Petit-lancy (CH); Giorgio Zoia, Lausanne (CH); Daniele Renzi, Lausanne (CH)

(73) Assignee: Genomsys SA, Lausanne (CH)

( * ) Notice: Subject to any disclaimer, the term of this patent is extended or adjusted under 35 U.S.C. 154(b) by 1119 days.

(21) Appl. No.: 16/341,419

(22) PCT Filed: Jul. 11, 2017

(86) PCT No.: PCT/US2017/041579
§ 371 (c)(1),
(2) Date: Apr. 11, 2019

(87) PCT Pub. No.: WO2018/071078
PCT Pub. Date: Apr. 19, 2018

(65) Prior Publication Data
US 2020/0043570 A1 Feb. 6, 2020

(30) Foreign Application Priority Data

Oct. 11, 2016 (WO) .................. PCT/EP2016/074297
Oct. 11, 2016 (WO) .................. PCT/EP2016/074301
(Continued)

(51) Int. Cl.
*G16B 50/50* (2019.01)
*G16B 30/10* (2019.01)
(Continued)

(52) U.S. Cl.
CPC ............. *G16B 50/50* (2019.02); *G16B 30/10* (2019.02); *H03M 7/3086* (2013.01); *H03M 7/40* (2013.01); *H03M 7/6005* (2013.01)

(58) Field of Classification Search
None
See application file for complete search history.

(56) References Cited

U.S. PATENT DOCUMENTS 6,303,297 B1  10/2001  Lincoln et al.
6,865,168 B1   3/2005  Sekine
(Continued)

FOREIGN PATENT DOCUMENTS

WO   2008100206 A1   8/2008
WO   2014145503 A2   9/2014
(Continued)

OTHER PUBLICATIONS

Choudhury, O.; Hazekamp, N. L.; Thain, D.; Emrich, S. Accelerating Comparative Genomics Workflows in a Distributed Environment with Optimized Data Partitioning; IEEE: Chicago, IL, USA, 2014; pp. 711-719.*

(Continued)

*Primary Examiner* — Soren Harward
(74) *Attorney, Agent, or Firm* — David B. Tingey; Bryant J. Keller; Kirton McConkie

(57) ABSTRACT

Method and apparatus for the coding and selective access of compressed genomic sequence data produced by genomic sequencing machines. The coding process is based on aligning sequence reads with respect to pre-existing or constructed reference sequences, on classifying and coding the sequence reads by means of sets of descriptors, and further partitioning the descriptor sets into access units of different types. Efficient selective access to specific genomic regions with the guarantee of retrieving all sequence reads mapped (Continued)

to those regions, is provided by: signaling the type of data mapping configuration used to store or transmit the descriptor sets, determining the minimum number of access units that need to be retrieved and decoded to access a genomic region, providing a master index table that contain all information for optimizing the data access process.

28 Claims, 17 Drawing Sheets

(30) Foreign Application Priority Data

| | | |
|---|---|---|
| Oct. 11, 2016 | (WO) | PCT/EP2016/074307 |
| Oct. 11, 2016 | (WO) | PCT/EP2016/074311 |
| Feb. 14, 2017 | (WO) | PCT/EP2017/017841 |
| Feb. 14, 2017 | (WO) | PCT/EP2017/017842 |

(51) Int. Cl.
　　*H03M 7/30*　　(2006.01)
　　*H03M 7/40*　　(2006.01)

(56) References Cited

U.S. PATENT DOCUMENTS

| | | |
|---|---|---|
| 2004/0023231 A1 | 2/2004 | Abu-Khabar et al. |
| 2004/0153255 A1 | 8/2004 | Ahn |
| 2006/0136144 A1 | 6/2006 | Kamentsky |
| 2008/0077607 A1 | 3/2008 | Gatewood et al. |
| 2009/0270277 A1 | 10/2009 | Glick et al. |
| 2011/0087437 A1 | 4/2011 | Casey et al. |
| 2012/0059670 A1 | 3/2012 | Sanborn et al. |
| 2013/0204851 A1 | 8/2013 | Bhola et al. |
| 2013/0332133 A1 | 12/2013 | Horn et al. |
| 2014/0371109 A1 | 12/2014 | van Rooyen et al. |
| 2014/0379270 A1 | 12/2014 | Park |
| 2015/0032711 A1 | 1/2015 | Kunin |
| 2015/0227686 A1 | 8/2015 | Sheinin et al. |
| 2016/0156367 A1 | 6/2016 | Kalevo et al. |
| 2016/0191076 A1 | 6/2016 | Leighton et al. |

FOREIGN PATENT DOCUMENTS

| | | |
|---|---|---|
| WO | 2014186604 A1 | 11/2014 |
| WO | 2015197201 A1 | 12/2015 |
| WO | 2016012105 A1 | 1/2016 |

OTHER PUBLICATIONS

Herzeel, C.; Costanza, P.; Decap, D.; Fostier, J.; Reumers, J. ElPrep: High-Performance Preparation of Sequence Alignment/Map Files for Variant Calling. PLoS One 2015, 10 (7), e0132868:1-16.*
Kutlu, M.; Agrawal, G. Page: A Framework for Easy PArallelization of GEnomic Applications; IEEE: Phoenix, AZ, USA, 2014; pp. 72-81.*
Mohamed, N. M. Data-Intensive Biocomputing in the Cloud. MS Thesis, Virginia Polytechnic Institute, Blacksburg, VA, 2013.*
Barnett, D. et al., "BamTools: a C++ API and toolkit for analyzing and managing BAM files", Bioinformatics, 2011, vol. 27 No. 12, pp. 1691-1692.
Cram-dev@ebi.ac.uk, "CRAM format specification, version 2.1", Mar. 14, 2014, https//github.com/samtools/hts-specs.
Samtools-devel@lists.sourceforge.net, "CRAM format specification (version 3.1)", Jun. 1, 2015, https://github.com/samtools/hts-specs.
samtools-devel@lists.sourceforge.net, "CRAM format specification, version 3.0", Sep. 8, 2016, https://samtools.github.io/hts-specs/CRAMv3.pdf.
HDF5, Jul. 2003, https://support.hdfgroup.org/ftp/HDF5/current/src/unpacked/release_docs/HISTORY-1_0-1)8_0_rc3.txt.
Hsi-Yang Fritz, M., "Efficient storage of high throughput DNA sequencing data using reference-based compression", Genome Research, 2011, vol. 21, pp. 734-740.
"Htslib Library Version 1.3", Dec. 15, 2015, https://github.com/samtools/htslib/releases/tag/1.3.
Idioa Ochoa, et al., "Aligned Genomic Data Compression via Improved Modeling", Bioinformatics Computer Biol., Dec. 2014, Issue 12.
Information Sciences Institute, "Internet Protocol DARPA Internet Program Protocol Specification", Sep. 1981, https://tools.ietf.org/html/rfc791.
Layer, R., "Getting samtools/bcftools to work with S3", Apr. 27, 2016, https://ryanmlayer.wordpress.com/2016-04-27/getting-samtoolsbcftools-to-work-with-s3.
Mohamed, N. et al., "Accelerating Data-Intensive Genome Analysis in the Cloud", 5$^{th}$ International Conference on Bioinformatics and Computational Biology, Mar. 2013.
Mousa, H. "DNA-Genetic Encryption Technique", I.J. Computer Network and Information Security, Jul. 2016, www.mecs-press.org.
"Multiplexing", Wikipedia, Sep. 17, 2016, XP002771498, https://en.wikipedia.org/wiki/index/php?title=Multiplexing&oldid=739917170.
"PacBio Alignment File Format (cmp.h5) Specification", 2015, https://pacbiofileformats.reathedocs.io/en/3.0/legacy/CmpH5Spec.html.
"Samtools—Utilities for the Sequence Alignment/Map (SAM) format"; Manual samtools-1.3 released Dec. 15, 2015, http://www.htslib.org/doc/samtools-1.3.html.
"Sequence Alignment/Map Format Specification", May 2013, master version available at https://github.comm/samtools/hts-specs.
The SAM/BAM Format Specification Working Group, "Sequence Alignment/Map Format Specification", Nov. 18, 2015, XP055387586, https://web.archive.org/web/20160505133503/http%3A//samtools.github.io/hts-specs/SAMv1.pdf.
The SAM/BAM Format Specification Working Group, "Sequence Alignment/Map Format Specification", Jan. 30, 2019, https://web.archive.org/web/20160505133503/http%3A//samtools.github.io/hts-specs/SAMv1.pdf.
Wtsi-npg/npg_ranger, Sep. 2016, http://github.com/wtsi-npg/npg_ranger.
Anonymous, "CRAM format specification, version 3.0", Sep. 8, 2016, XP002771305, retrieved from the Internet on Jun. 22, 2017 at https://samtools.github.io/hts-specs/CRAMv3.pdf.
Jens Panneel, "Implementation and optimization of CABAC in a genomic data compression framework with support for random access", Masters dissertation, Faculty of Engineering and Architecture, Jan. 1, 2015 (Jan. 1, 2015), pp. 1-81, XP055535469, retrieved from the Internet Dec. 17, 2018 at https://lib.ugent.be/fulltxt/RUG01/002 /224/797/RUG01-002224797 2015 0001_AC.pdf.

* cited by examiner

Since the mapping positions of both Read n and Read Pair m are at a distance from the AU$_i$ end that is smaller than GRL$_n$ and GRL$_m$, some bases belonging to Read n and Read Pair m map in regions belonging to the following AUs ranges

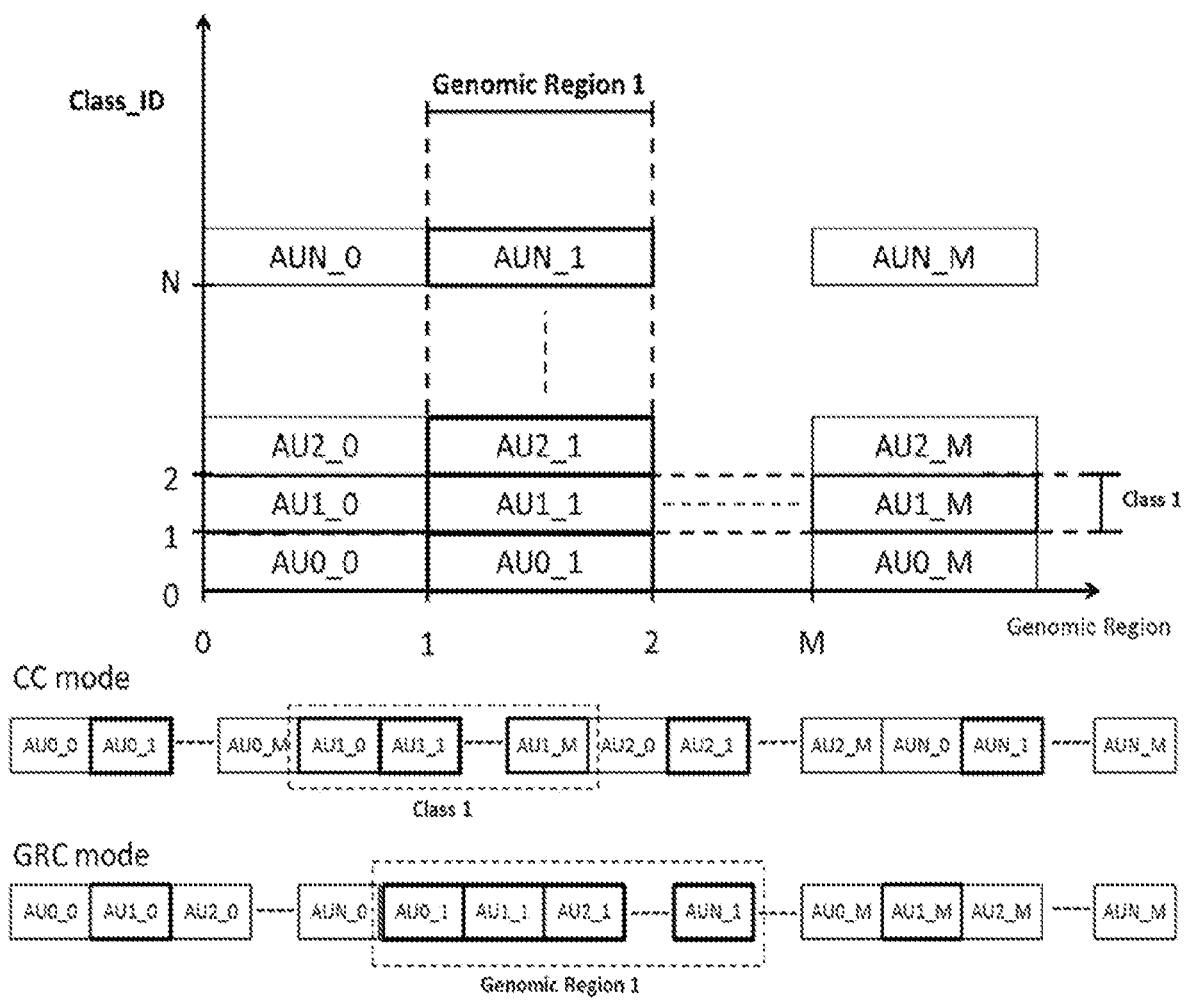

Figure 17

| Data_type = 0/1 | Sequence 1 | | Sequence 2 | | ... | Sequence J | | |
|---|---|---|---|---|---|---|---|---|
| | 1 | ... | N1 | 1 | ... | N2 | ... | 1 | ... | Nj |
| Class P | Ps11, Pe11 | ... | Ps1N1, Pe1N1 | Ps21, Pe21 | ... | Ps2N2, Pe2N2 | ... | PsJ1, PeJ1 | ... | PsJNj, PeJNj |
| Class N | Ns11, Ne11 | ... | Ns1N1, Ne1N1 | Ns21, Ne21 | ... | Ns2N2, Ne2N2 | ... | NsJ1, NeJ1 | ... | NsJNj, NeJNj |
| Class M | Ms11, Me11 | ... | Ms1N1, Me1N1 | Ms21, Me21 | ... | Ms2N2, Me2N2 | ... | MsJ1, MeJ1 | ... | MsJNj, MeJNj |
| Class I | Is11, Ie11 | ... | Is1N1, Ie1N1 | Is21, Ie21 | ... | Is2N2, Ie2N2 | ... | IsJ1, IeJ1 | ... | IsJNj, IeJNj |
| Class HM | HMs11, HMe11 | ... | HMs1N1, HMe1N1 | HMs21, HMe21 | ... | HMs2N2, HMe2N2 | ... | HMsJ1, HMeJ1 | ... | HMsJNj, HMeJNj |
| Class U | Indexes for unmapped reads. Not relying on reference sequences | | | | | | | | | |

Figure 18

METHOD AND APPARATUS FOR THE ACCESS TO BIOINFORMATICS DATA STRUCTURED IN ACCESS UNITS

CROSS-REFERENCE TO RELATED APPLICATIONS

This application claims priority to and the benefit of Patent Applications PCT/EP2016/074311, PCT/EP2016/074301, PCT/EP2016/074307, PCT/EP2016/074297, PCT/US2017/17842, PCT/US2017/17841.

TECHNICAL FIELD

This disclosure provides a novel method for the efficient selective access to compressed genome sequencing data structured in access units which improves the compression performance, reduces the volume of data that needs to be accessed, reduces the algorithmic complexity of the decoding process, and improves the sequence data access performance by providing new efficient functionality that are not available with known prior art methods of representation.

BACKGROUND AND SUMMARY OF THE INVENTION

An appropriate representation of genome sequencing data is fundamental to enable efficient genomic analysis applications such as genome variants calling and all other analysis performed with various purposes by processing the sequencing data and metadata.

Human genome sequencing has become affordable by the emergence of high-throughput low cost sequencing technologies. Such opportunity opens new perspectives in several fields ranging from the diagnosis and treatment of cancer to the identification of genetic illnesses, from pathogen surveillance for the identification of antibodies to the creation of new vaccines, drugs, and the customization of personalized health treatments.

Hospitals, genomic analysis providers, bioinformatics and large biological data storage centers are looking for affordable, fast, reliable and interconnected genomic information processing solutions which could enable scaling genomic medicine to a world-wide scale. Since data storage and data access have become major bottlenecks in the usage of sequencing data, methods for representing genome sequencing data in compressed form are increasingly investigated.

The most used genome information representations of sequencing data are the FASTQ format for raw genomic sequences and SAM (Sequence Alignment Mapping) format for genomic sequences mapped to a reference genome. These are text-based formats conceived when the genomic information was scarce and precious and users wanted to be able to read and manually edit the sequenced data. FASTQ is based on the notion of record. Each FASTQ record is composed by four sections where the first is devoted to a string that identifies the record (read name or read identifier), the second section represents the sequence of nucleotides composing the read, the third section is a separator (typically represented by the character '+') and the fourth section (having exactly the same length as the second) contains sequencing quality scores representing the degree of confidence the sequencing process had when "calling" each nucleotide.

The most used compression approaches to information represented as FASTQ and SAM rely on the use of general purpose algorithms such as LZ (from Lempel and Ziv, the authors who published the first versions) schemes (the well-known zip, gzip etc). When general purpose compressors such as gzip are used, the result of compression is usually a single blob of binary data. The information in such monolithic form results quite difficult to archive, to transfer and to process particularly in the case of high throughput sequencing for which the volume of data are extremely large. The BAM format is characterized by poor compression performance due to the fact that it just applies generic entropy coding to the redundant and poorly structured SAM format rather than extracting the actual essential genomic information contained in the SAM format. For such reason, applying general purpose text compression algorithms such as "gzip" rather than exploiting the specific nature of each data source (the genomic data itself) results to be a very inefficient compression approach.

BAM supports selective access to data by means of the creation of an external index which contains offsets of data blocks in the compressed files overlapping genomic regions represented by bins. A hierarchical bins structure is used in BAM indexing where each bin overlaps a specific genomic interval. Each bin is either non-overlapping or completely contained by other bins. The main drawback of this approach is that:

The index file is external to the content and needs to be calculated and managed as a separate resource. This is not efficient in terms of data manipulation and processing because the information contained in the index file is redundant with information already contained in the data file.

Bin size is restricted to six values ($2^{29}$, $2^{26}$, $2^{23}$, $2^{20}$, $2^{17}$ or $2^{14}$). This limits the flexibility of selective access to genomic regions that can be identified only by using these six values.

According to the specific structure of binning and indexes, the selective access to genomic regions with the guarantee that all reads mapped to them are correctly retrieved, may require several file seek calls (e.g. calls to functions moving the file read pointer to a desired position) to make sure that all reads overlapping the requested interval are actually retrieved.

A less used approach to genomic data compression than BAM, but more sophisticated and more efficient, is CRAM. CRAM provides more efficient compression for the adoption of differential encoding with respect to a reference (it partially exploits the data source redundancy), but it still lacks several features such as the possibility of incremental updates, the support for streaming and the selective access to specific classes of compressed data. Better compression of genomic data provided by CRAM format versus BAM is obtained by the adoption of different algorithms according to the specific type of data to be encoded. Therefore, it is considered as a step forward compared to BAM, even if it is still lacking an appropriate source modelling stage to be associated to the entropy coding stage.

Concerning data manipulation, CRAM files indexing is implemented by means of an external index file that is constituted by a gzipped tab delimited file, containing 6 columns describing the data blocks overlapping each genomic region of the encoded genomic data. The main drawbacks of such indexing approach are:

The index file is external to the content and needs to be calculated and managed as a separate resource, like in the case of BAM. Such technical solution is not efficient in terms of storage, data manipulation and processing because the information contained in the index file is redundant with the information already contained in the data file.

The index is gzipped as a single blob, therefore the access to even a small genomic region requires unzipping and parsing the whole file.

A gzipped tab separated format, whereas human readable when unzipped, is not an efficient format to be parsed and processed by machines.

The described state of the art approaches generate poor compression ratios and data structures that are difficult to navigate and manipulate once compressed. Downstream analysis can be very slow due to the necessity of handling those large and rigid data structures even to perform simple operation and particularly to access selected regions of the genomic dataset.

CRAM relies on the concept of the CRAM record. Each CRAM record represents a single mapped or unmapped reads by coding all the elements necessary to reconstruct it. In particular CRAM approach to sequence data compression presents the following drawbacks and limitations:

CRAM does not support data indexing and random access to data subsets sharing specific features. Data indexing is out of the scope of the specification (see section 12 of CRAM specification v 3.0) and it is implemented as a separate file. Conversely the approach of the invention described in this document employs a data indexing method that is integrated with the encoding process and indexes are embedded in the encoded (i.e. compressed) bit streams.

CRAM is built by core data blocks that can contain any type of mapped reads (perfectly matching reads, reads with substitutions only, reads with insertions or deletions (also referred to as "indels")). There is no notion of data classification and grouping of reads in classes according to the result of mapping with respect to a reference sequence. This means that all data need to be inspected even if only reads with specific features are searched. Such limitation is solved by the invention disclosed in this application by classifying and partitioning data in classes before coding.

CRAM is based on the concept of encapsulating each read into a "CRAM record". This implies the need to inspect each complete "record" when reads characterized by specific biological features (e.g. reads with substitutions, but without "indels", or perfectly mapped reads) are searched.

Conversely, in the present invention there is the notion of data classes coded separately in separated information layers and there is no notion of record encapsulating each read. This enables more efficient access to set of reads with specific biological characteristics (e.g. reads with substitutions, but without "indels", or perfectly mapped reads) without the need of decoding each (block of) read(s) to inspect its features.

In a CRAM record each record field is associated to specific information flags and each flag must always carry the same information as there is no notion of context since each CRAM record can contain any different type of data. This coding mechanism introduces redundant information and prevents the usage of efficient context based entropy coding.

Instead, in the present invention, there is no notion of flag denoting data because this is intrinsically defined by the information "layer" the data belongs to. This implies a largely reduced number of symbols to be used and a consequent reduction of the information source entropy which yields higher compression performance. Such improvement is possible because the use of different "layers" enables the encoder to reuse the same symbol across each layer with different meanings according to the context. In CRAM each flag must always have the same meaning as there is no notion of contexts and each CRAM record can contain any type of data.

In CRAM, substitutions, insertions and deletions are represented by using different syntax elements, option that increases the size of the information source alphabet and yields higher source entropy. Conversely, the approach of the disclosed invention uses a single alphabet and encoding for substitutions, insertions and deletions. This makes the encoding and decoding process simpler and produces a lower entropy source model which coding yields bitstreams characterized by high compression performance.

The invention disclosed in this document introduces several innovative elements that yield high performance compression and provide an efficient selective access to the sequence reads and to the associated information (or only to parts thereof) directly in the compressed domain. So as to achieve such new features, not available in the current practice, the invention, at the encoder side, is characterized by the following elements:

1. Sequence reads are aligned and mapped onto pre-existing or constructed reference sequences.
2. Reads are classified according to the result of the mapping process into classes and sub-classes (i.e. reads that perfectly match a reference sequence segment, that match with only a type of mismatch, that match with a bounded number of mismatches of given types, etc, etc, . . . , . . . as described in detail in the following sections.
3. According to their classifications, sequence reads, and their associated alignment information, are represented by means of a specific subset of "descriptors" that are entropy coded to achieve high compression efficiency (i.e. each class is represented by a specific and "minimal" subset of descriptors whose set of values for a specific read is also called "genomic record").
4. Within each class, the coded subsets of descriptors (i.e. the genomic records) are further partitioned into an ordered list of data units called Access Units characterized by the boundaries of the genomic region to which the sequence reads represented by the compressed genomic records are mapped.
5. The partitioning into Access Units for each Dataset, is performed according to one of two distinct modes: a) a non-overlapping mode (i.e. the genomic regions associated to Access Units do not overlap), b) an overlapping mode (i.e. the genomic region associated to one Access Unit may overlap with the genomic region associated to other Access Units). In the non-overlapping mode the Access Units are ordered according to the increasing value of both coordinates (start and end) of the genomic region they are associated. In the overlapping mode the Access Units are ordered according to the increasing value of the start coordinate (i.e. the smallest value of the coordinate of the associated genomic region).
6. The type of partitioning used by the encoder for compressing and structuring the sequence reads into Access Units, overlapping or non-overlapping mode, is registered as a field of the Dataset Header for the complete Dataset. This information fields is used by a decoding device, to optimize the selective access procedure to retrieve the required data in the two cases when Access Units are accessed after having been stored into a file system or streamed to a client.

In the case of paired sequence reads, in addition to all steps listed from item 1 to 6 the following elements are also used in the coding procedure;

1. Sequence read pairs and the associated alignment information are represented as single elements by a specific subset of descriptors (i.e. a single genomic record is used for each sequence pair) and included in a single Access Unit for achieving high performance compression.
2. Read pairs exceeding the Access Units boundaries and characterized by a pair length beyond given parameter values defined for each reference sequence, are instead split, represented as single reads by two subset of descriptors, coded and included into different Access Units according to their respective mapping positions.

The values of the coding parameters used, by the encoder to determine if reads pairs have to be coded as single entity in the same Access Unit or split into single reads and coded into two distinct Access Unit, are registered into Dataset Header fields. A different coding parameter can be used per each reference sequence. This information enables the minimization of the number of Access Units that are accessed and decoded when selective access to a genomic region in the compressed domain is required.

When the Access Units, after the coding stage, are stored into a file system the following steps are performed:

1. Data blocks composing the Access Units are stored into a file system according to two possible formats: a) the Descriptor Stream Contiguous (DSC) format in which data belonging to the same Descriptor are structured into streams and are stored in contiguous areas of the storage device, b) the Access Unit Contiguous (AUC) format in which data belonging to different descriptors, but belonging to the same Access Unit are stored in contiguous areas of the storage device.
2. In case the AUC data format is used for the data storage, data contiguity can be implemented in two different modes: a) class-based with all Access Units of the same class stored in the same area of the storage device, (Class Contiguous mode, CC), b) genomic-region-based, with all Access Units mapping to the same genomic region stored in the same area of the storage device, (Genomic Region Contiguous mode, GRC).
3. The information about the Access Unit storage format employed to store a dataset into a file system, DSC or AUC/CC or AUC/GRC is registered in a field of the Dataset Header so that the information is available when data are retrieved and decoded to optimize the data access process. The AUC data format is of particular interest for the minimization of file system accesses in case of region-based selective access, as it enables storing data belonging to the same Access Unit in contiguous areas of the storage device. In the case of AUC data format, the CC mode results more efficient when accessing data of any subsets of the different class, whereas the GRC mode result efficient when accessing data of all classes mapping to the same genomic region. Conversely, the DSC format results efficient for some other use cases, such as for instance when one or more Descriptors Streams are protected by applying an encryption algorithm, in which case data contiguity of the Descriptor Stream makes protection and access operations more efficient.
4. The information characterizing the genomic region associated to the data contained into the Access Units is stored and is available into a multidimensional data structure called Master Index Table that is structured as follows:
    a. The position, as number of nucleotides, of the left-most matching base among all reads or read pairs contained in the Access Unit, with regards to the reference sequence.
    b. The position, as number of nucleotides, of the right-most matching base among all reads or read pairs contained in the Access Unit, with regards to the reference sequence.
    c. The lists of access unit sizes (when the AUC mode is used)
    d. The list of offsets, expressed as number of bytes, of the first byte of each descriptor data block of each Access Unit, with respect to the first byte of the Dataset payload.

At data retrieving side, when the Access Units have been stored in a file system in compressed form and selective access to any sub-set the descriptors mapped on a specified genomic region is required, the following steps are performed;

1. The decoder fetches from the appropriate Dataset Header fields the information specifying;
    a. The mode by which the genomic data has been partitioned into the AUs stored in the file system: non-overlapping mode or overlapping mode
    b. The format used to store the data of all AUs in the filesystem: DSC or AUC/CC or AUC/GRC
2. With the information obtained at step 1, by accessing and processing the information stored in the MIT all AUs containing data satisfying the selective access request are identified
3. The minimum number of AUs, the minimum number of data blocks by using a minimum number of file access calls is used to retrieve all data that satisfy the selective data access request.
4. The minimum volume of data is decoded to satisfy the selective data access request.

In the case of Access Units carrying paired reads descriptors in addition to the steps at point 1 and 2, the coding parameters used to decide when read pairs are not coded as single entity, but the reads are separated and coded into two distinct AUs is fetched from the Dataset Header for each reference sequence. Such parameters are used to identify the minimum number of AUs that need to be retrieved and decoded to satisfy the selective access request and guarantee that all reads of the split pairs are correctly retrieved.

At client side, when the Access Units are streamed to a client in compressed form and selective access to any sub-set the descriptors mapped on a specified genomic region is required, the following step is performed:

1. The decoder fetches from the Transport Block Header the information specifying the class of data and the range covered by the AU to decide if the AU has to be decoded to answer the selective access request or can be ignored.

In the case of Access Units carrying paired reads descriptors in addition to the steps at point 1, the coding parameter used to decide when read pairs are not coded as single entity, but the reads are separated and coded into two distinct AUs is fetched from the Dataset Header. Such parameters are used to identify if the incoming AU needs to be decoded to satisfy the selective access request.

BRIEF DESCRIPTION OF THE DRAWINGS

FIG. 17 shows the two ways of storing Access Units of the same class of data on a filesystem. Using the AUC/CC and AUC/GRC modes. Using the AUC/CC mode the blocks of data belonging to the same data class are stored contiguously. Using the AUC/GRC mode the data blocks of different data classes, but belonging to the same genomic region are stored contiguously. On the vertical axis are reported the different data classes identified by a specific identifier (Class_ID), on the horizontal axis the different contiguous genomic regions.

FIG. 18 shows the Master Index Table storing the AU Start Positions ($Cs_{jk}$) and End Positions ($Ce_{jk}$) partitioned per data classes.

SUMMARY

Figure 1:
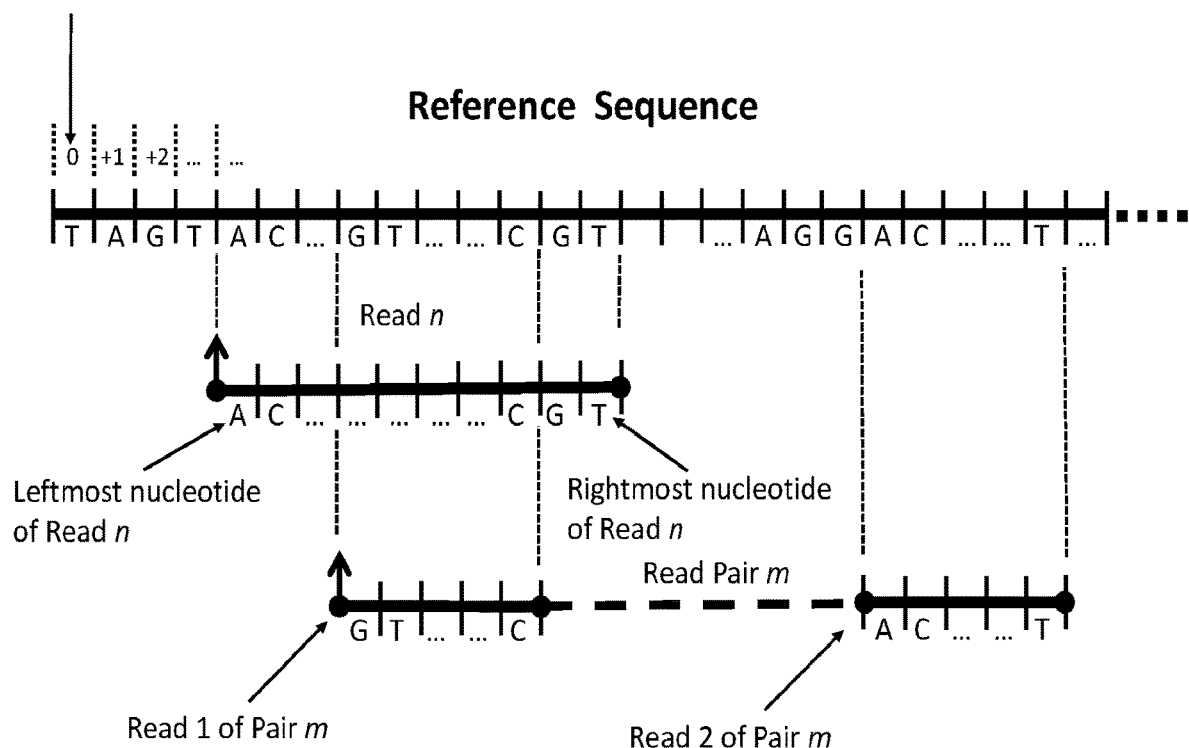
FIG. 1 shows the coordinate system on a Reference Sequence and how reads and read pairs are mapped on a Reference Sequence.
Figure 2:
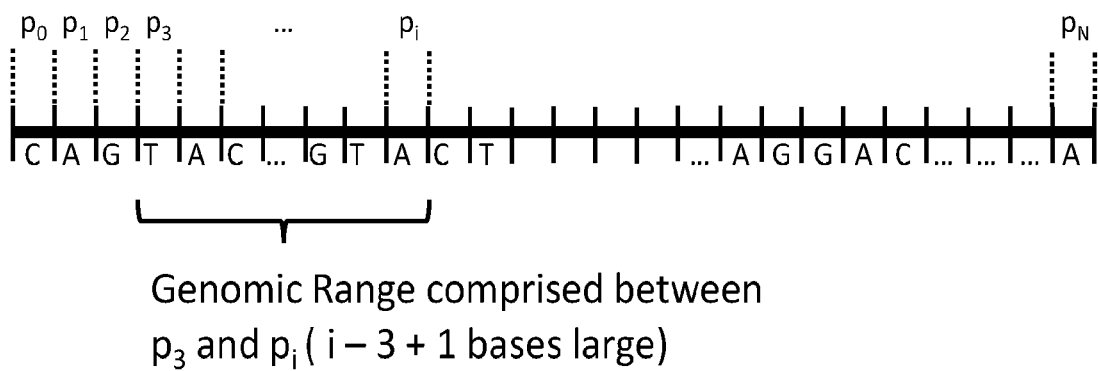
FIG. 2 shows how the coordinates on a reference sequence are also referred to as positions of bases on a reference.
Figure 3:
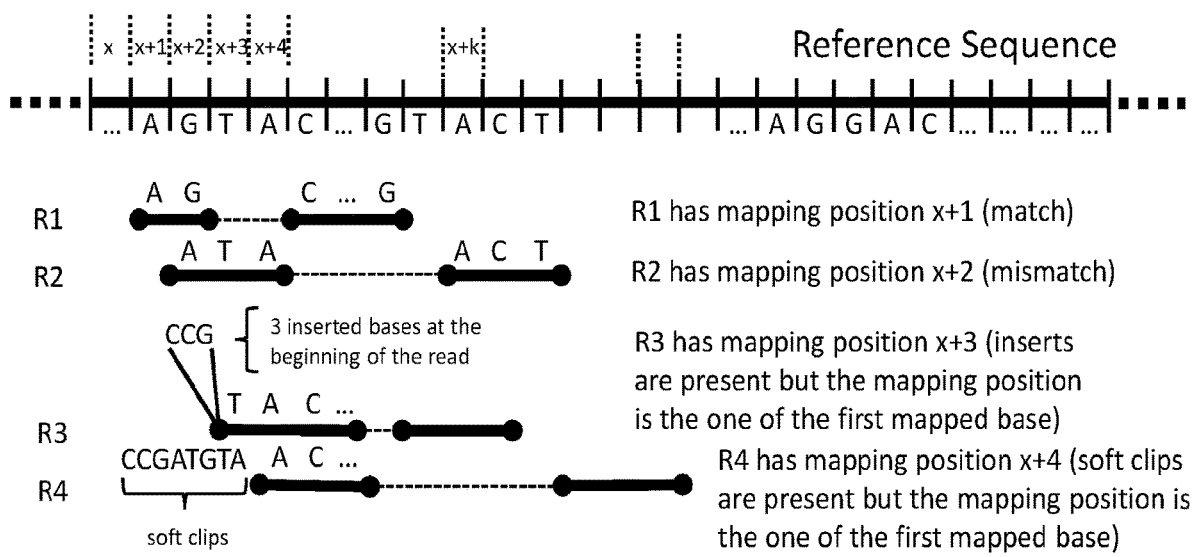
FIG. 3 shows the definition of mapping positions for genomic records.
Figure 4:
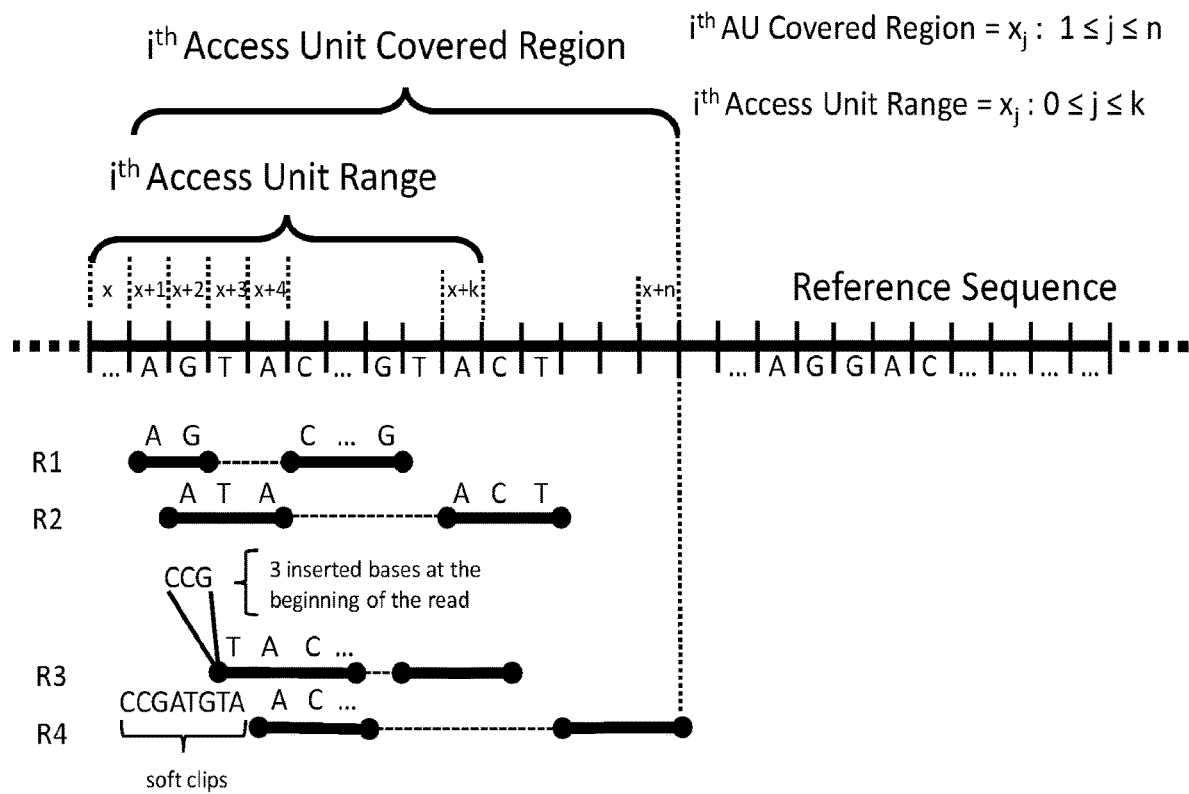
FIG. 4 shows the definition of Access Unit Range and Covered Region in relation to Genomic Record positions.

The features of the claims below solve the problem of existing prior art solutions by providing a method for selectively accessing a genomic region in a file, said file being arranged into entropy coded Access Units $AU_i$, said method comprising the steps of:
extracting values of start coordinate $s_i$ and end coordinate $e_i$ of said Access Units $AU_i$ from an indexing table contained in the file and disjointly coded from said $AU_i$ for the case of file stored information
further comprising extracting a threshold value MaxD from the genomic dataset header (1602) of said file, wherein said threshold value MaxD specifies the maximum value that the pairing distance of read pairs can assume, when read pairs are present in said file.

In another aspect of the selective access method said indexing table contains the classes of Access Units in order to selectively identify the entropy coded Access Units according to the classes of data by employing a vector of pointers, without having to entropy decode said Access Units In another aspect of the selective access method said $AU_i$ comprise a range information named Access Unit range, said Access Unit range representing the genomic range comprised between the AU start position and the right most genomic record position of all genomic records contained in said AU In another aspect of the selective access method said Access Units can be of two different modes:
- a first mode in which blocks of data from different descriptors of the same AU are stored contiguously
- a second mode in which data blocks belonging to the same descriptors but belonging to different Access Units are stored in contiguous regions of the file In another aspect of the selective access method said mode information is coded in a field of a parameter set and comprised into the genomic dataset header In another aspect of the selective access method said first mode can be further represented in two additional different sub-modes:
- a first sub-mode wherein all $AU_i$ of the same class are stored contiguously in the file
- a second sub-mode wherein $AU_i$ of the same genomic regions are stored contiguously in the file In another aspect of the encoding method said indexing table contains the following information:
- a positional information, expressed as number of nucleotides, of the left-most mapped base among all reads or read pairs contained in the Access Unit, with regards to the reference sequence.
- a positional information, expressed as number of nucleotides, of the right-most mapped base among all reads or read pairs contained in the Access Unit, with regards to the reference sequence.
- a list of offsets, expressed as number of bytes, of the first byte of each descriptors data block of each Access Unit, with respect to the first byte of the Dataset payload.
- list of descriptor stream sizes, when said first mode is used
- list of Access Unit sizes, when said second mode is used.

In another aspect of the selective access method, for the case of streaming information, the values of start coordinate $s_i$ and end coordinates $e_i$ of said Access Units $AU_i$ are extracted from the header of each Access Unit $AU_i$.

In another aspect of the selective access method said distance of read pairs is expressed as a number of bases or coordinates in a reference system.

A method for coding genomic data comprising genomic regions, said genomic data being arranged into entropy coded Access Units $AU_i$, said method comprising the steps of:
- coding values of start coordinate $s_i$ and end coordinate $e_i$ of said Access Units $AU_i$ in an indexing table disjointly coded from said Access Units for the case of storing information in a file
- further coding a threshold value MaxD in the genomic dataset header (1602) of said file, wherein said threshold value MaxD specifies the maximum value that the pairing distance of read pairs can assume, when read pairs are present in said genomic data to be coded.

In another aspect of the coding method said indexing table further contains the mapped classes of Access Units such that at the decoder it is possible to selectively identify the entropy codedAccess Units according to the classes of data by employing a vector of pointers, without having to entropy decode said Access Units In another aspect of the coding method said $AU_i$ comprise a range information named Access Unit range, said Access Unit range representing the genomic range comprised between the AU start position and the right most genomic record position of all genomic records contained in said AU In another aspect of the coding method said AU can be of two different modes:
- a first mode in which blocks of data from different descriptors of the same AU are stored contiguously
- a second mode in which data blocks belonging to the same descriptors but belonging to different Access Units are stored in contiguous regions of the file In another aspect of the coding method said mode information is coded in a field of a parameter set and comprised into the genomic dataset header In another aspect of the coding method said first mode can be further represented in two additional different sub-modes:
- a first sub-mode wherein all $AU_i$ of the same class are stored contiguously in the file
- a second sub-mode wherein Access Units of the same genomic regions are stored contiguously In another aspect of the coding method said indexing table contains the following information:
- a positional information, expressed as number of nucleotides, of the left-most mapped base among all reads or read pairs contained in the Access Unit, with regards to the reference sequence.
- a positional information, expressed as number of nucleotides, of the right-most matching base among all reads or read pairs contained in the Access Unit, with regards to the reference sequence.
- a list of offsets, expressed as number of bytes, of the first byte of each descriptor data block of each Access Unit, with respect to the first byte of the Dataset payload.
- list of descriptor stream sizes when said first mode is used
- list of access unit sizes when said second mode is used.

In another aspect of the coding method said distance of read pairs is expressed as a number of bases or coordinates in a reference system A method for decoding compressed coded genomic data comprising genomic regions, said coded genomic data being arranged into entropy coded Access Units $AU_i$, said method comprising the steps of:
- parsing values of start coordinate $s_i$ and end coordinate $e_i$ of said Access Units $AU_i$ from an indexing table disjointly coded from said Access Units for the case of information stored in a file
- further parsing a threshold value MaxD from the genomic dataset header (1602) of said file, wherein said threshold value MaxD specifies the maximum value that the pairing distance of read pairs can assume, when read pairs are present in said genomic encoded data.

In another aspect of the decoding method said indexing table further contains the mapped classes of Access Units such that it is possible to selectively identify the entropy coded Access Units according to the classes of data by employing a vector of pointers, without having to entropy decode said Access Units In another aspect of the decoding method said access units comprise a range information named Access Unit range, said Access Unit range representing the genomic range comprised between the AU start position and the right most genomic record position of all genomic records contained in said AU In another aspect of the decoding method said AU can be of two different modes:
- a first mode in which blocks of data from different descriptors of the same AU are stored contiguously
- a second mode in which data blocks belonging to the same descriptors but belonging to different Access Units are stored in contiguous regions of the file In another aspect of the decoding method said mode information is parsed from a field of a parameter set and comprised into the genomic dataset header In another aspect of the decoding method said first mode can be further represented in two additional different sub-modes:
- a first sub-mode wherein all $AU_i$ of the same class are stored contiguously in the file
- a second sub-mode wherein Access Units of the same genomic regions are stored contiguously In another aspect of the decoding method said indexing table contains the following information:
- a positional information, expressed as number of nucleotides, of the left-most mapped base among all reads or read pairs contained in the Access Unit, with regards to the reference sequence.
- a positional information, expressed as number of nucleotides, of the right-most mapped base among all reads or read pairs contained in the Access Unit, with regards to the reference sequence.
- a list of offsets, expressed as number of bytes, of the first byte of each descriptor data block of each Access Unit, with respect to the first byte of the Dataset payload.
- list of descriptor stream sizes when said first mode is used
- list of Access Unit sizes when said second mode is used.

In another aspect of the decoding method said distance of read pairs is expressed as a number of bases or coordinates in a reference system.

A computer-readable medium comprising instructions that when executed cause at least one processor to perform said selective access method.

A computer-readable medium comprising instructions that when executed cause at least one processor to perform said coding method.

A computer-readable medium comprising instructions that when executed cause at least one processor to perform said decoding method.

Support data storing genomic data encoded according to said encoding method.

A file format wherein genomic data are encoded according to said encoding method.

A file encoded according to said coding method wherein the coded information are encrypted.

An apparatus for selective access of said encoded genomic information comprising means for executing said selective access steps.

DETAILED DESCRIPTION

The genomic or proteomic sequences referred to in this invention include, for example, and not as a limitation, nucleotide sequences, Deoxyribonucleic acid (DNA) sequences, Ribonucleic acid (RNA), and amino acid sequences. Although the description herein is in considerable detail with respect to genomic information in the form of a nucleotide sequence, it will be understood that the methods and systems for compression can be implemented for other genomic or proteomic sequences as well, albeit with a few variations, as will be understood by a person skilled in the art.

Genome sequencing information is generated by High Throughput Sequencing (HTS) machines in the form of sequences of nucleotides (a. k. a. "bases") represented by strings of letters from a defined vocabulary. The smallest vocabulary is represented by five symbols: {A, C, G, T, N} representing the 4 types of nucleotides present in DNA namely Adenine, Cytosine, Guanine, and Thymine. In RNA Thymine is replaced by Uracil (U). N indicates that the sequencing machine was not able to call any base and so the real nature of the nucleotide at that position is undetermined.

In case the IUPAC ambiguity codes are adopted by the sequencing machine as vocabulary, the alphabet used for the symbols is composed of the following symbols: {A, C, G, T, U, W, S, M, K, R, Y, B, D, H, V, N or -}.

In the context of the present invention a "Genomic Dataset" is defined as any structured set of genomic data including, for example, genomic data of a living organism, one or more sequences and metadata generated by the genomic sequencing of a living organism or by any other step of genomic data processing performed on the original sequencing data.

The nucleotides sequences produced by sequencing machines are called "reads". Sequence reads can be composed of a number of nucleotides ranging between a few dozens to several thousand. Some sequencing technologies produce sequence reads composed of "pairs" of which one read is originated from one DNA strand and the other is originated from the other strand. A read associated to another read in a sequencing process producing pairs is said to be its "mate".

Throughout this disclosure, a reference sequence is a sequence of nucleotides associated to a mono-dimensional integer coordinate system for which each integer coordinate is associated to a single nucleotide. Coordinate values can only be equal or larger than zero. This coordinate system in the context of this invention is zero-based (i.e. the first nucleotide has coordinate 0 and it is said to be at position 0) and linearly increasing from left to right.

When mapping sequence reads on a reference sequence, said reference sequence is used as axis of a mono-dimensional coordinate system in which the left-most position is denoted as position 0. In a sequence read, mapped to a reference sequence, the nucleotide composing the read mapped at the reference sequence position identified by the smallest coordinate number is usually referred to as the "left-most" nucleotide, whereas the nucleotide composing the read mapped at the reference sequence position identified by the largest coordinate number is referred to as the "right-most" nucleotide. See also FIG. 1. Throughout this disclosure, a nucleotide is also referred to as a "base".

When a sequence read is mapped to a reference sequence, the coordinate of the left-most mapped base is said to represent the mapping position of the read on the reference sequence.

A reference genome is composed by one or more reference sequences and it is assembled by scientists as a representative example of a species' set of genes. For example GRCh37, the Genome Reference Consortium human genome (build 37) is derived from thirteen anonymous volunteers from Buffalo, N.Y. However, a reference sequence could also consist of a synthetic sequence conceived and merely constructed to improve the compressibility of the reads in view of their further processing.

Throughout this disclosure, a genomic record is defined as a coded representation of
- either a single sequence read or a paired sequence read optionally associated with alignment information, read identifier and quality values
- a reference sequence (e.g. a chromosome) or a portion thereof.

Throughout this disclosure, a genomic record position is defined as the position on the reference sequence of the left-most mapped base of the read or read pair coded in a genomic record.

Mapped bases in a read or read pair record are intended as:
  bases of the aligned read that match the corresponding base on the reference sequence
  bases of the aligned read that do not match the corresponding base (a.k.a. Single Nucleotide Polymorphism)
  Bases present in the aligned read and not present in the reference sequence (a.k.a. insertion), and bases preserved by the alignment process, but not mapped on the reference sequence (a.k.a. soft clips) do not correspond to any mapping positions.

In this disclosure, the read composing a read pair with a base mapping on the smallest coordinate on a reference is referred to as "Read 1" whereas its mate is referred to as "Read 2".

The distance, expressed as number of nucleotides (or bases), or coordinates, separating two reads generated as a pair, by a sequencing machine using today technology, is unknown, and it is determined by mapping both reads composing the pair (i.e. minimizing appropriate matching functions) to a reference sequence.

Throughout this disclosure, a genomic record length is defined as the distance between the left-most mapped base coded in the record and the right-most mapped base coded in the record.

Figure 5:
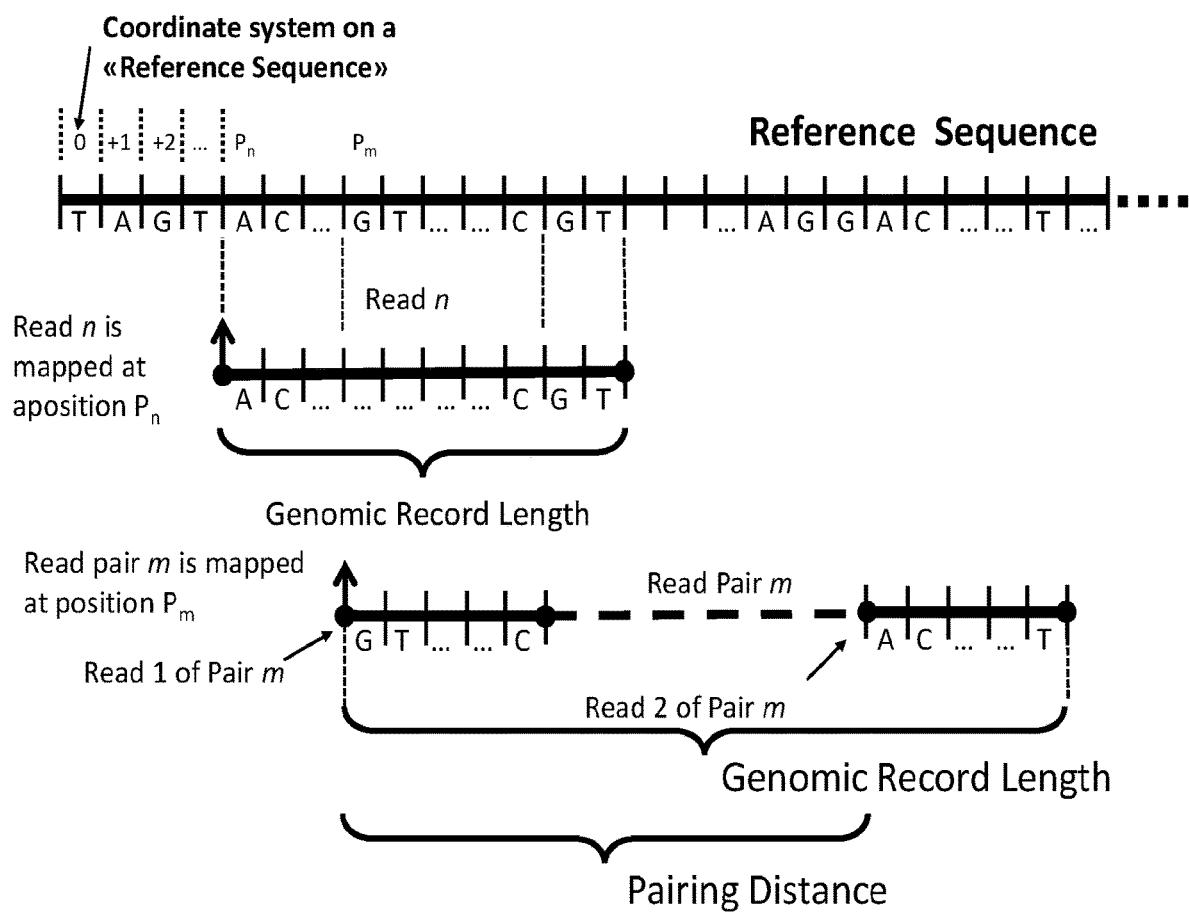
FIG. 5 shows how that Genomic Record Length is defined as the number of genomic positions on a reference sequence separating the left-most mapped base from the right-most mapped base of a read or read pair. In case of read pairs this is the number of genomic position on the reference sequence separating the left-most base of read 1 from the right-most base of its mate read 2 when both reads are mapped on the same reference sequence. The "Pairing Distance" is defined as the difference between the left-most position of Read1 and the left-most position of Read2.
Figure 6:
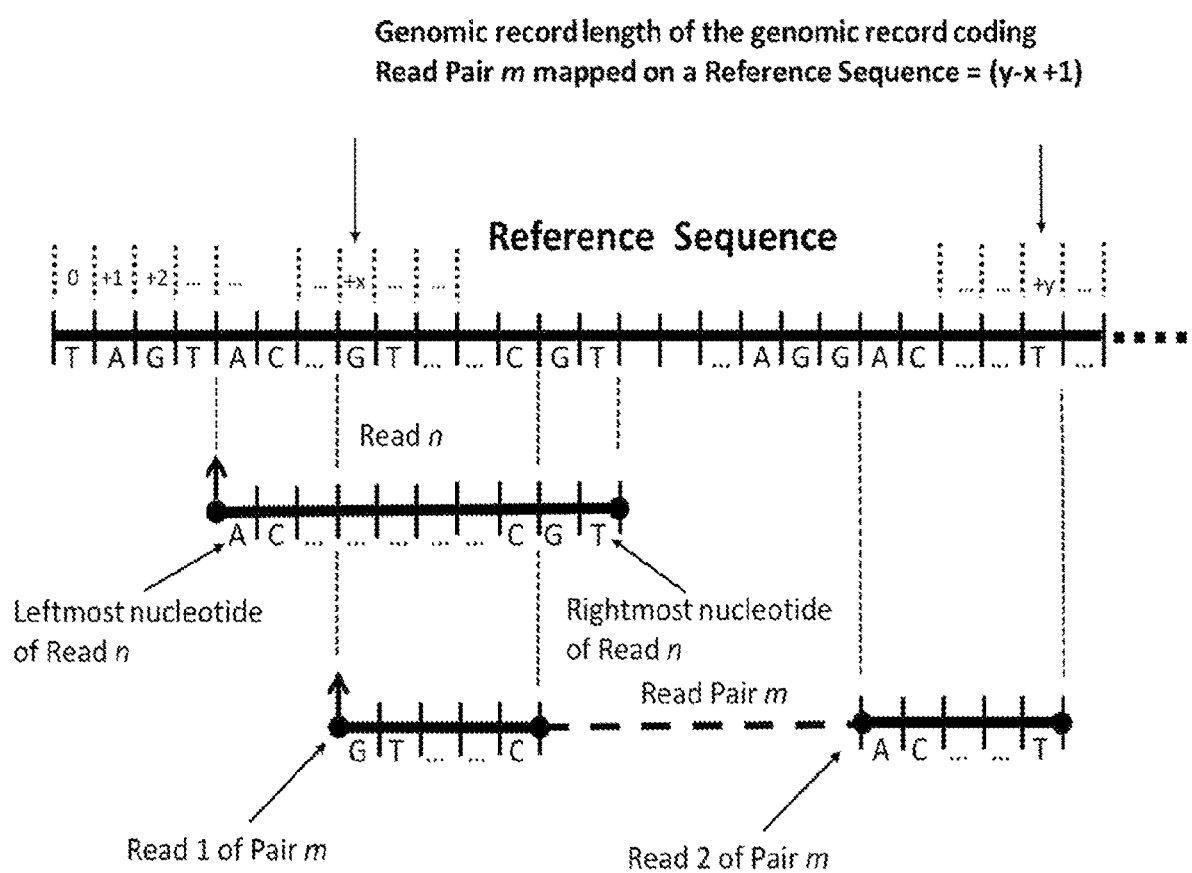
FIG. 6 shows an example an example of calculation of the Genomic Record Length.

In the case of read pairs in which both reads are mapped on the same reference and coded in the same genomic record, the pairing distance is defined as the distance between the left-most mapped base of Read1 and the left-most mapped base of Read2. An example of pairing distance is shown in FIG. 5.

Throughout this disclosure, in the case of single reads the genomic record length (GRL) is defined as the integer obtained by subtracting the mapping position of the left-most base from the mapping position of the right-most mapped base and adding "1".

GRL=(right-most base position)−(left-most base position)+1

Throughout this disclosure, in the case of read pairs, the genomic record length (GRL) is defined as the integer obtained by subtracting the mapping position of the left-most base of the read mapping at the smallest position on a reference sequence (Read 1) from the coordinate of the mapping position of the right-most base of its mate (Read 2) and adding "1". Such definition of genomic record length is illustrated in FIG. 5.

Throughout this disclosure, in the case of genomic record encoding a reference sequence or a portion thereof, the genomic record length is defined as the number of nucleotides composing the encoded sequence.

Throughout this disclosure, a Genomic Range is defined as a contiguous set of coordinates on a reference sequence defined by a start coordinate S and an end coordinate E such that S E. The start and end position of a genomic range are always included in the genomic range.

This invention aims at defining a new method enabling the efficient access to aligned genomic sequence reads mapped to any genomic region when the sequence reads are compressed by means of sets of descriptors included into a number of data blocks called Access Units.

Throughout this disclosure, an Access Unit (AU) is defined as a logical data structure containing a coded representation of genomic information or related metadata structured to facilitate the data access and manipulation. It is the smallest data structure that can be decoded by a decoding device implementing the invention described in this disclosure.

According to the type of coded information carried by the AU, it can be decoded either independently of any other AU or using information contained in other AUs.

AUs can be of several types according to the nature of the coded data. An Access Unit contains either a reference sequence, or a portion thereof, or encoded reads or read pairs belonging to a single class of data. Classes of reads are defined according to the matching results of the read or read pair versus a reference sequence.

For example an Access Unit may contain the entire chromosome 1 of GRCh37, the Genome Reference Consortium human genome (build 37). Another Access Unit may contain the coded representation of nucleotides of chromosome 1 of GRCh37 that are located between coordinates 50'000 and 150'000. Another Access Unit may contain only reads or read pairs that perfectly map on the reference sequence without any mismatch. Another Access Unit may contain reads or read pairs that only contain "N" symbols as mismatches with respect to the reference sequence. Another Access Unit may contain reads or read pairs that contain any type of substitutions (e.g. one base present in the read or read pair is different from the base at the corresponding mapping position in the reference sequence). Another Access Unit may contain reads or read pairs that contain mismatches, insertions, deletions and soft clipped bases. Another Access Unit may contain only read or read pairs that do not map on the reference sequence. Another Access Unit may contain only read pairs in which one read is mapped and the other is not mapped on the reference sequence. Another type of Access Unit may contain only encoded segments of a reference genome composed by one or more reference sequences (for example chromosomes).

The essential characteristic of an Access Unit is that it contains in compressed form all elements needed to reconstruct the genomic information (sequence reads or read pairs, reference sequences), associated alignment information and metadata of reads or read pairs it represents. In other words, to fully reconstruct the reads, read pairs or reference sequence and associated information carried by an Access Unit it is only necessary to retrieve the Access Unit itself and, when needed, the Access Units containing the reference sequence it refers to.

In each Access Unit the descriptors listed in the next section representing the encoded read or read pairs are aggregated in separate data blocks—one per type—in order to exploit their homogeneous statistical properties when entropy coding is applied to compress them.

Each Access Unit contains the compressed sub-set of descriptors representing sequence reads or read pairs belonging to the same class mapped to a genomic region on a reference sequence. Such genomic region on the reference sequence is defined by a start coordinate (or start position) and an end coordinate (or end position).

Descriptors are syntax elements representing part of the information necessary to reconstruct (i.e. decode) coded reference sequences, sequence reads and the associated mapping information or pairs of sequence reads and associated mapping information. Different types of descriptors are defined to express:
  the mapping position of a read on a reference sequence,
  the distance between a read and its mate,
  the length of a sequence read,
  the position of mismatches in aligned reads with respect to reference sequences, the types of mismatches with respect to reference sequences at the associated positions, the bases that could not be mapped on the reference sequence by the mapping procedure and are classified as "soft clipped" bases, the sequence reads lengths, the mapping flags as specified by the SAM specification, the multiple mapping positions that are associated to a single read or read pair by the mapping procedure, the identification of the existence of spliced reads (i.e. reads that when split in chunks find mapping positions with higher degrees of matching accuracy then when they are mapped as single connected read mapped on a single position on a reference sequence)

the specific type of reference sequence used such as:
  reference genomes as those published by consortia like the Genome Reference Consortium (e.g. GRCh37), the University of California Santa Cruz (e.g. hg19),
  reference sequences built by using specified sets of reads and specified sets of assembly rules, the positions and types of modifications applied to reference sequences with the objective of reducing the entropy of the descriptors used to represent the mismatches of sequence reads mapped on such modified reference sequences, the representation of sequence reads that cannot be mapped at any position of the reference sequence with specified degrees of matching accuracy, the representation of entire reference sequences or portions thereof.

The complete list and the precise definition of each descriptor referred to in this disclosure, and used by this invention is provided in the following sections.

As mentioned above, several descriptors are used by this invention to represent in compressed form reference sequences, sequence reads or read pairs so that they can be fully reconstructed with their associated information. In case reads or read pairs are also classified and separated into different classes, according to the results of the mapping on reference sequences, and entropy coded into separate data blocks, different sub-sets of descriptors are used for representing each class or reads or read pairs. Therefore an Access Unit contains only those entropy coded descriptors that are needed to represent either a reference sequences—or portions thereof—or reads or read pairs belonging to the same class. This is shown in FIG. 12 for read of variable length and FIG. 11, FIG. 13, FIG. 14 and FIG. 15 for read pairs of constant length.

Throughout this disclosure, an Access Unit Start Position is defined as the left-most Genomic Record Position among all Genomic Records contained in the Access Unit.

Throughout this disclosure, an Access Unit End Position is defined as the right-most mapped base position among all mapped bases of all Genomic Records contained in the Access Unit Throughout this disclosure, the Access Unit Range is defined as the Genomic Range comprised between the AU Start Position and the right-most genomic record position among all genomic records contained in the Access Unit. The number of positions (or coordinates) contained in a Genomic Range can be calculated by subtracting the AU Start Position from the AU End Position and adding "1".

Throughout this disclosure, the Access Unit Covered Region is defined as the Genomic Range comprised between the AU Start Position and the AU End Position.

Throughout this disclosure, an Access Unit is also said to cover the genomic region between its Start Position and its End Position.

Figure 8:
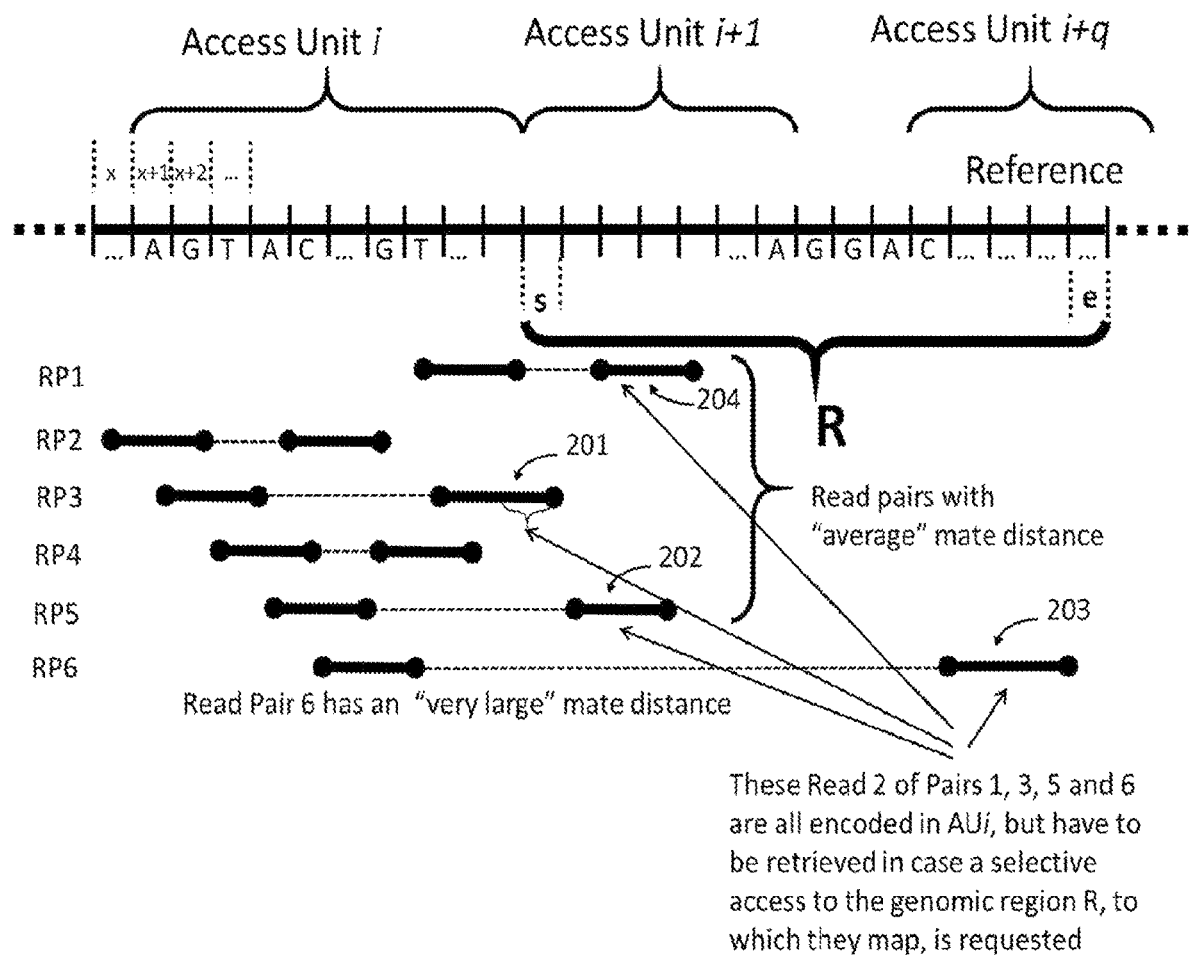
FIG. 8 shows how the fact that read pairs map on genomic regions spanning over different Access Units Ranges requires that the selective access procedure must be capable of identifying all Access Units that may contain genomic records mapping on the genomic region R specified by the selective access request.

Genomic records contained in an AU can only have mapping position at a distance from the AU end position that is smaller than the genomic record length. However it may occur that bases belonging to the read or read pair coded in the genomic record result mapped in genomic regions covered by a different AUs. The occurrence of such case is illustrated in FIG. 8.

The fact that a portion of a read or read pair, or a complete Read 2 of a pair, may be mapped on a genomic region that does not belong to the range of the Access Unit which contains their compressed representation (i.e. the associated entropy coded sub-set of descriptors) is a problem whenever it is required to retrieve all reads or read pairs that map on a specific genomic region. Such operation is very common in many genomic analysis applications and needs to be implemented with a very high efficiency to avoid the necessity of inspecting all Access Units composing a data set to be sure to have retrieved all the requested reads. This invention disclosure addresses the problem of providing a method that yields high compression performance for read and read pairs and also provides a new solution to the problem of also guaranteeing to access all reads mapped with at least one base on any genomic region of interest, by accessing and decoding the minimum number of Access Units or, which is equivalent, the smallest volume of data.

According to the definitions provided above two useful ways of building Access Units can be identified:
1. A "non-overlapping mode" in which the genomic ranges of Access Units of the same data class never overlap
2. An "overlapping mode" in which the genomic ranges of Access Units of the same data class may overlap The "non-overlapping mode" is preferable in scenarios when genomic data are compressed and stored in memory as files as well as in streaming scenarios when stored files are streamed from one storage device to another since it enables the implementation of more efficient selective access procedures. The "overlapping mode" supports streaming scenarios when portions of the genomic datasets become available for coding into Access Units and transmission before the entirety of the genomic sequence data is available at the transmitting device.

Compressed Representation of Genomic Sequence Reads and Reference Sequences

A common element of efficient approaches to genomic sequence reads compression is the exploitation of the correlation of sequence data with respect to a reference sequence. Even if the somatic profile of the human population is extremely diversified, the actual portion of the number of nucleotides that differs from person to person is about only 0.1% of the total number of nucleotides composing an entire genome. Therefore, the specific genomic information characterizing each individual is very limited with respect to the entire information carried by an entire genome. When a pre-existing reference genome is available, be it for previous sequencing or as a published "average" consensus reference, the most efficient way to encode the actual information is to identify and encode only the differences with respect to the reference genome.

In order to do so with raw sequence reads in the form of FASTQ data, a preliminary pre-processing step of mapping on an available reference genome is performed. In case a reference genome is not available or if the bias introduced by the usage of a specific reference is not desirable, the construction of a new reference sequence by means of assembling the available sequence reads into longer sequences is a possible alternative.

When sequence reads have been mapped with respect to a pre-existing or to a constructed reference sequence, each sequence read can be fully represented by a number of elements denoted in this disclosure as "read descriptors" or simply "descriptors".

For example, in the case of a sequence read that perfectly matches a segment of a reference sequence, the only sub-set of descriptors needed to represent the sequence read is composed by the coordinate of the mapping position on the reference (usually the coordinate of the mapping position of the left-most base of the sequence read), the length of the sequence read itself and the information indicating if the read is mapping on the direct or reverse DNA strand with respect to the reference sequence strand.

In case it is not possible to find any mapping position for which all the bases of the sequence read match all bases of the reference sequence, the mapping (or mappings) with the minimal number of mismatches are retained. In such case a different sub-set of descriptors is needed to also express the substitutions, the insertions, the deletions and the clipped bases that may occur in correspondence of the mapping position with the minimal or close to minimal number of mismatches. With such sub-set of descriptors the sequence reads can be reconstructed using the information carried by the descriptors and the information carried by the reference sequence.

The mapping process can also produce other types of information such as: multiple possible mapping positions and related scores, the quality of mapping, the specification of spliced reads, the mapping on two different references (usually chromosomes) of reads belonging to a pair, features of the sequencing process (e.g. Polymerase Chain Reaction duplicates or optical duplicate). All such information requires specific additional descriptors that extend each sub-sets that then is compressed by applying for each sub-set of descriptors appropriate entropy coding algorithms.

The genome sequencing process can generate read duplicates (i.e. two or more exact copies of the same genomic sequence) due to:
the chemistry of the genome sequencing process (Polymerase Chain Reaction duplicate),
the data acquisition process (optical duplicate). A read is called as an optical duplicate if the pair of reads are both on the same tile, and the distance between reads is less than a given configuration parameter depending on the experiment.

Each read or read pair can therefore be uniquely represented by a specific sub-set of descriptors according to the results of the mapping process.

Commonly used approaches such as SAM and CRAM do not encode reads or read pairs according to the specific sub-set of descriptors needed to represent their mapping information (i.e. they do not classify sequence reads into data classes and do not code them separately into Access Units containing in compressed form only sequence reads belonging to a single data class. In the case of sequence read generated in pairs, state of the art approaches do not code them as single elements partitioned into classes as done by the invention described in this disclosure. Such state of the art approaches are characterized by the following limitations and drawbacks:
1. The coding of reads or reads pairs without classifying sequence reads into separate data classes according to mapping results versus a reference sequence and using a unique super-set of descriptors is an inefficient approach that yields poor compression performance.
2. The coding of read pairs as separate sequence reads requires the duplication of several descriptors carrying the same information, thus results inefficient and yields poor compression performance.
3. The retrieval of the information needed to reconstruct read pairs result to be complex and inefficient since the process requires a brute-force sequential search in possibly the entire dataset which as in case of next generation sequencing (NGS) technology can be extremely large.
4. The selective access to read or read pairs mapped to specific genomic regions requires to search the entire dataset to have the guarantee that all reads or read pairs are retrieved.

When coding read pairs by means of a single sub-set of descriptors, the following technical advantages are evident to a person skilled in the art:
1. The information common to both reads, which is clearly redundant, is not replicated by coding a pair as single element (e.g. read pair identifiers, mapping distance, mapping reference identifiers, the various mapping quality information currently encoded by specific flags in the SAM file format)
2. The retrieval of the mutual pairing information (i.e. the information providing which read is the mate of any read at hand) is straightforward and does not require any further processing. Conversely in the state of the art approaches it may require to parse the entire volume of data.

In order to enable efficient selective access to specific portions of sequencing data and being able to transport them on a digital data network, the set of descriptors used to represent sequence reads aligned to a reference are structured in logically separate and independent data blocks called Access Units (AU). Each Access Unit contains only the compressed representation of a single data class, and can be decoded either independently of any other Access Units or using only Access Units carrying the coded representation of the reference sequence region used for mapping. This enables selective access and out-of-order transport capabilities.

In order to increase the compression efficiency this invention eliminates the need of specifying the "mapping reference identifier" descriptor for each read pair having both pairs mapped on the same reference sequence. Each Access Unit can contain only reads or pairs that map on the same reference. Using such solution the descriptor representing the reference sequence identifier needs to be encoded only once per each Access Unit or set of Access Units (and not repeated for each read as currently done in SAM/BAM formats).

The only exception of the rule expressed above is the case of read pairs having the two reads mapped on different reference sequences (e.g. chromosomes). In this case the pair is split and the two reads are coded as two separate genomic records and each encoded read contains the identifier of the reference sequence its mate is mapped to.

A person skilled in the art knows that classifying information in groups of elements with homogeneous statistical properties provides better compression performance with respect to the usage of a general purpose compressor (e.g. LZ type algorithm) applied to a heterogeneous set of data. As a consequence, when encoding genomic sequence reads in pairs by means of a specific sub-set of descriptors, higher compression is achieved thanks to the lower entropy characterizing each separate sub-set of descriptors and higher processing efficiency when reconstructing and retrieving read pairs.

Sequence Reads Descriptors

This section introduces the descriptors specified to represent genomic sequence reads mapped on a reference sequence. The specific sub-set of descriptors used to represent each read or read pair depends on the result of the mapping versus a reference sequence (i.e. presence or absence of mismatches between the read, or read pair and the reference sequence).

Position

A read or read pair position is defined as the mapping position on the reference sequence of the left-most base in the read or read pair. A descriptor of type "position" is necessary per each read or read pair. The value of the "position" descriptor may represent:
- the value of the coordinate of the left-most base in the read or read pair on the reference sequence
- the difference with respect to the coordinate of the previous read or read pair coded in the same Access Unit.

A "position" descriptor is required to represent each encoded read or read pair.

In this invention disclosure such descriptor will be referred to as pos descriptor.

Reads Pairing

In case of read pairs, the descriptor that represents how each read is associated with its mate in the pair can be expressed by several syntax elements as it may represent:
- The difference of coordinate between a base of a read with the respective base in the mate (e.g. the left-most mapped base in a read with the left-most mapped base in the mate). In this invention disclosure such descriptor will be referred to as pair descriptor.
- The absolute coordinate of the mate on the reference sequence with the identifier of the reference sequence the mate maps to. Such representation option is used when:
  - the two reads of a pair map on different reference sequences (e.g. chromosomes) or
  - when the two reads of a pair map on the same reference, but are separated by a number of bases exceeding a given value which is specified to be the maximum likely admissible pairing distance.
  In this invention disclosure such descriptor will be referred to as abspair descriptor. In case of mate mapped on a different reference sequence the descriptor identifying the reference sequence is referred to as refid The number of encoded reads separating a read from its mate in case of paired reads. In this invention disclosure such descriptor will be referred to as pcount descriptor.

Maximum Pairing Distance

As already mentioned, the association between two reads is an information generated by the sequencing process, whereas the pairing distance is determined by the mapping process using a reference sequence. In the presence of values much larger than the likely size of a DNA fragment undergoing the sequencing process, for many reasons discussed in the following of this disclosure, it results more appropriate and more convenient to split the coding into two single reads and code them into separate Access Units. Obviously the information that the two reads have been generated as pair is maintained. This is obtained by defining a maximum value that the descriptors "pair" may assume for the overall dataset or in each Access Units depending on the genome region covered (i.e. for each chromosome). In other words a parameter MaxD is specified as maximum value that the descriptors "pair" may assume. The value of MaxD is expressed as a number of bases (or coordinates in a reference sequence) and it is used by an encoder to determine the specific sub-set of descriptors to be used to encode a read pair as single unit in the same Access Units or as separate reads in different Access Units.

The reads of a pair are encoded using sub-sets of descriptors values according to three possible cases:
1. the two reads are mapped on the same reference sequence and the difference between the coordinates of the leftmost base is smaller or equal to the parameter MaxD,
2. the two reads are mapped on the same reference sequence and the difference between the coordinate of the leftmost base is larger than the parameter MaxD,
3. the two reads are mapped on different reference sequences (e.g. different chromosomes).

In case a read is not coded as single entity special reserved values of the pairing distance are used to represent such information. These descriptors are called "distance flags", are listed and explained in Table 2.

To cover the cases listed above the pair descriptors are specified as follow:

TABLE 1

Values of pairing distance descriptors for each mapping case and in function of the parameter MaxD.

| Pairing distance: "pair" | | Absolute coordinate: "abspair" | Reference identifier: "refid" |
| --- | --- | --- | --- |
| pair ≤ MaxD | pair > MaxD | Present only for distance flags 1, 2, 3 and 4 as specified below | Present only for distance flags 3 and 4 as specified below |
| distance expressed as number of bases between read 1 and read 2 | distance flag as specified below. | Indicates the absolute coordinate of the read on the same reference sequence as the other in the pair or on the sequence identified by the next field "reference identifier" | A unique identifier for a reference sequence. |

The admissible values of the distance flags and associated semantics are provided in the table below:

TABLE 2

Distance flags definition and associated sematic.

| Distance flags | Meaning | Followed by |
|---|---|---|
| flag1 | Read 2 of the pair is mapped on the same reference sequence and "pair" > MaxD | Read 2 absolute coordinate on the reference sequence |
| flag2 | Read 1 of the pair is mapped on the same reference sequence, and "pair" > MaxD | Read 1 absolute coordinate on the reference sequence |
| flag3 | Read 2 of the pair is mapped on a different reference sequence | Read 2 absolute coordinate on the reference sequence and reference sequence identifier |
| flag4 | Read 1 of the pair is mapped on a different reference sequence | Read 1 absolute coordinate on the reference sequence and reference sequence identifier |
| flag5 | The first read (i.e. from file no. 1 in a FASTQ file pair) is not paired | N/A |
| flag6 | The second read (i.e. from file no. 2 in a FASTQ file pair) is not paired | N/A |
| flag7 | Single reads | N/A |

Examples of the use of the pairing distance descriptors to encode read pairs are provided in the section below.

1) Read 1 and Read 2 of the same pair are mapped on chromosome X (ID==22) and the absolute coordinate of read 2 on chromosome X is 155249594

| Pairing distance | Absolute coordinate | Reference identifier |
|---|---|---|
| flag3 = 1 | 155249594 | 22 |

2) Read 1 and read 2 of the same pair are mapped on the same reference sequence with a pairing distance of 1548961 ("pair">MaxD). Read 2 is mapped at coordinate 32567499 on the reference sequence.

| Pairing distance | Absolute coordinate | Reference identifier |
|---|---|---|
| flag1 | 32567499 | not present |

3) Read 1 and read 2 of the same pair are mapped on the same reference sequence with a pairing distance of 353 positions ("pair"<MaxD)

| Pairing distance | Absolute coordinate | Reference identifier |
|---|---|---|
| 353 | not present | not present |

4) Read 1 is unpaired

| Pairing distance | Absolute coordinate | Reference identifier |
|---|---|---|
| flag5 | not present | not present |

In this disclosure the set of descriptors representing a form of pairing distance are also referred to as pair descriptors.

It has to be underlined that splitting read pairs and encoding them as separate reads whenever the pairing distance exceed specified values, may appear contradictory with the objective claimed above of achieving high compression performance. In reality the values of the pairing distance obtained by large and statistically meaningful sets of experimental data obtained by current sequencing technologies, present Gaussian distributions centered at the value of a few hundred bases. The number of pairs that presents pairing distance values of a few Sigma are in the order of fractions of 1% of the overall data. Therefore, the splitting of such small fraction of pairs produces negligible reductions of coding efficiency, but enables very large factors of reduction of access bandwidth and very high increases of overall speed for selective access operations to specific genomic regions.

Read Length

In the case of reads with variable length, a descriptor per read is used to represent the length expressed as the number of nucleotides composing the read. Obviously, a read length descriptor is required per each read only in the case of variable read length.

In this disclosure this descriptor is also referred to as rlen descriptor.

Reverse Complement

The DNA is composed by a double helix in which each strand is the complement of the other since Adenine ('A') only couples with Thymine ('T') and Cytosine ('C') only couples with Guanine ('G'). Therefore, it is only necessary to represent one strand to know the nucleotide composition of the other. This is the reason for which reference sequences are always represented by a single sequence, and mapping tools are capable of finding mapping positions for reads belonging to both strands. If a read is mapped on the complementary strand of the DNA helix, it is said to be "reverse complemented". A descriptor is necessary to carry such information and carries the information indicating if the original read is the reverse complement or not of the reference sequence it is mapped to.

A reverse complement descriptor is required per each read.

In this disclosure such descriptor is also referred to as rcomp descriptor.

Unknown Bases Positions

During the sequencing process it may occur that the machine is unable to call any base at a given positions of a read or read composing a pair. Such event is identified by a special symbol 'N' at the corresponding read position. A descriptor identifying each occurrence of an 'N' symbol in a read is thus needed.

The descriptor may represent:

The absolute position of the 'N' symbol in read or read of a pair expressed as coordinate of the reference sequence, The relative position of the previous 'N' in the same read or read of a pair.

In this disclosure such descriptor is also referred to as nmis descriptor.

Mismatches Position and Type

Sequence reads mapped on a reference sequence may present mismatches with respect to the reference sequence segment they are mapped to. These mismatches can be classified and are denoted as substitutions, deletions or insertions according to the following cases:

The presence of a different nucleotide (base) with respect to the reference sequence (substitution)

The absence of a nucleotide in the mapped read (deletion)

The presence of a nucleotide in the read that is not present in the reference (insertion)

The representation of each mismatch type implies the use of three descriptors, one representing the mismatch position in the read or read pair (also referred to as mmpos), another representing the type of mismatch when only substitutions are present (also referred to as subtype) and another representing the type of mismatch when substitutions, insertions and deletions are present (also referred to as mmtype).

Soft Clips

Genomic sequence reads mapped on a reference sequence may present at their edges portions of the sequence of nucleotides that do not match any or just a few of those present on the reference sequence at the mapping position. These sequences portions are called soft-clips and can be represented by a descriptor simply composed by the string of symbols representing the bases of the sequence portion.

Reads can admit only one or two soft clips, at the beginning of the read and/or at the end.

In this document such descriptor is also referred to as sclips descriptor.

Mapping Flags

Mapping flags are used to carry specific information relative to the alignment process such as:

The presence of multiple mapping position for a read or read pair

The presence of spliced reads

The presence of PCR (Polymerase Chain Reaction) or optical duplicates

Supplementary alignment (used in case the aligner has produced several possible mapping position for the same read or read pair)

The read fails the quality check (i.e. technology vendor specific procedure to measure the quality of the sequencing process)

In this document such descriptors are also referred to as flags descriptors.

Unmapped Reads

In case reads or both reads of pairs are not mapped at any position of the reference sequences the reads or read pairs are classified as unmapped. In such case the reads are represented by descriptors constituted by the verbatim sequence of symbols representing the read. The reads are partitioned into Access Units belonging to a separate class of data that obviously cannot be selectively accessed by specifying a genomic region.

Encoding Reads or Read Pairs without Mismatches

In case reads or read pairs perfectly map on the reference sequence (i.e. without any mismatch) the following sub-set of descriptors is needed to reconstruct the read and associated mapping information:

A position descriptor per read or read pair (pos)

A reverse complement descriptor per read or two per read pair (rcomp)

A length descriptor per read (in case of variable length reads only) (rlen)

A pairing descriptor per read pair (pair)

A set of mapping flags (flags)

In this invention such read or read pair is classified as belonging to Class P.

The position descriptor pos represents the position on the reference genome of the left-most mapping base of the read or read pair.

The reverse complement descriptor rcomp indicates whether a read is mapped on the direct or reverse strand of the reference sequence.

In case of variable length reads a descriptor rlen provides the read length.

The pair descriptor carries the information necessary to reconstruct the entire pair. The syntax of the descriptor is provided in Table 1.

Figure 11:
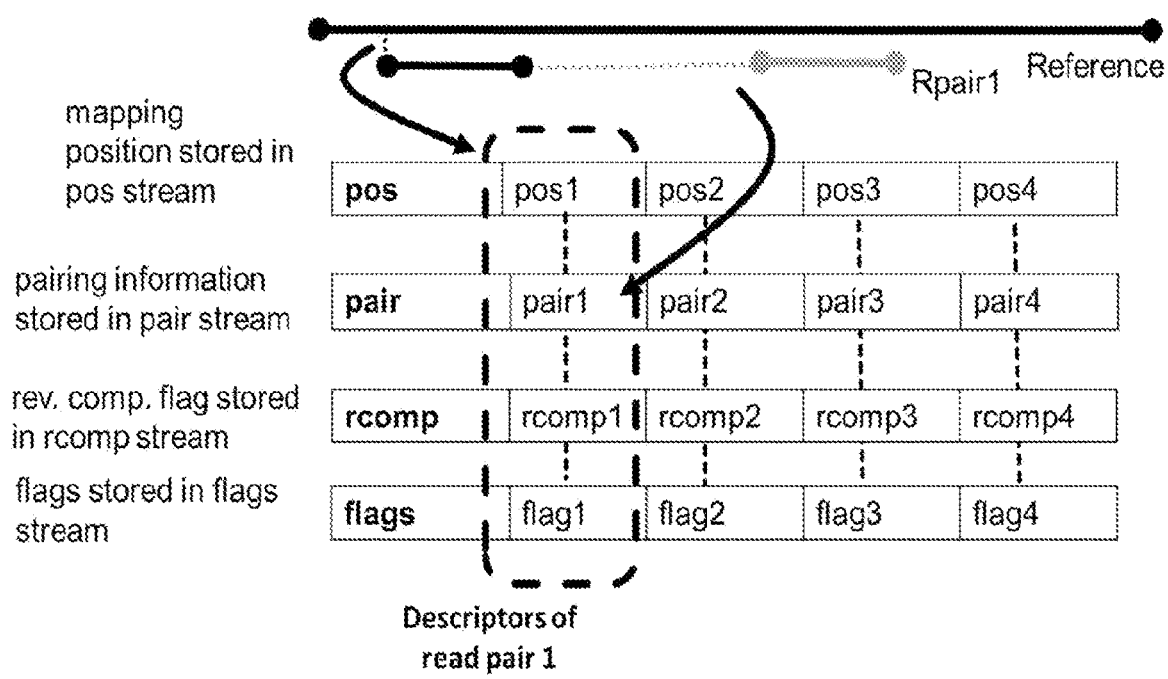
FIG. 11 shows the descriptors used to encode a pair of constant length reads perfectly mapping on the reference sequence (Class P).
Figure 12:
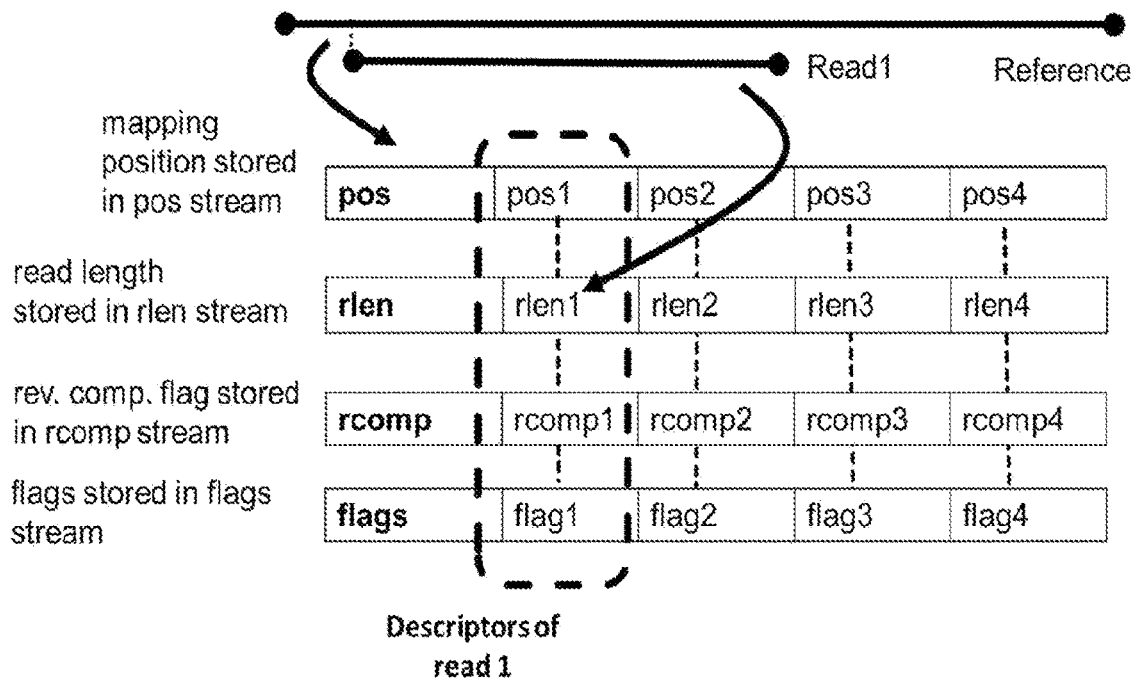
FIG. 12 shows the descriptors used to encode a read of variable length perfectly mapping on the reference sequence (Class P)

An example of the encoding of a read pair belonging to Class P is provided in FIG. 11, the corresponding example for a single read of variable length is provided in FIG. 12.

Encoding read or read pairs with mismatches represented only by unknown bases

In the case a read or read pair maps on the reference sequence, but contains at least one unknown base, the following sub-set of descriptors is needed to reconstruct the read and associated mapping information:

A position descriptor per read or read pair (pos)

A reverse complement descriptor per read or two per read pair (rcomp)

A position per each unknown base (nmis)

A length descriptor per read (in case of variable length reads only) (rlen)

A pairing descriptor per read pair (pair)

A set of mapping flags (flags)

Descriptors already present in Class P sub-set have the same syntax and semantics. The additional descriptor nmis provides the position in a read (pair) of the bases called as "unknown" by the sequencing process (symbol 'N').

In this invention such read or read pair is classified as to belonging to Class N.

Figure 13:
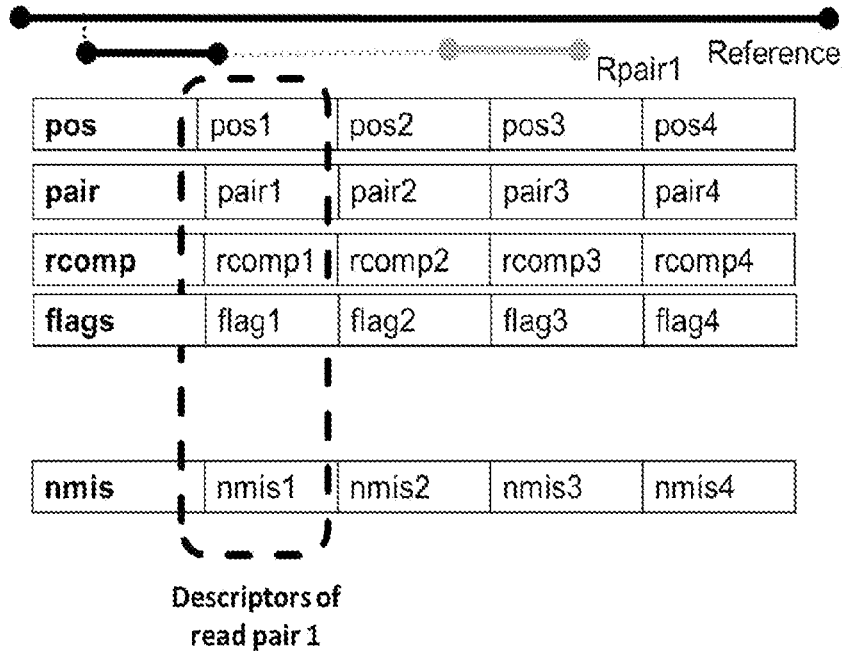
FIG. 13 shows the descriptors used to encode a pair of constant length reads with unknown bases with respect to the reference sequence (Class N).

An example of the encoding of a read pair of Class N is provided in FIG. 13.

Encoding Read or Read Pairs with Unknown Bases and Substitutions

In the case a read or a read pair maps on the reference sequence and presents at least one substitution, but no deletions or insertions, the following sub-set of descriptors is needed to reconstruct the read and associated mapping information:

A position descriptor per read or read pair (pos)

A reverse complement descriptor per read or two per read pair (rcomp)

A descriptor per each substitution position (mmpos)

A descriptor per each substitution type (subtype)

A position per each unknown base (nmis)

A length descriptor per read (in case of variable length reads only) (rlen)

A pairing descriptor per read pair (pair)

A set of mapping flags (flags)

Descriptors already present in class P sub-set have the same syntax and semantics. The additional descriptors used for such sequence read data class are mmpos to represent the position of substitutions and subtype to represent the type of substitution.

Figure 14:
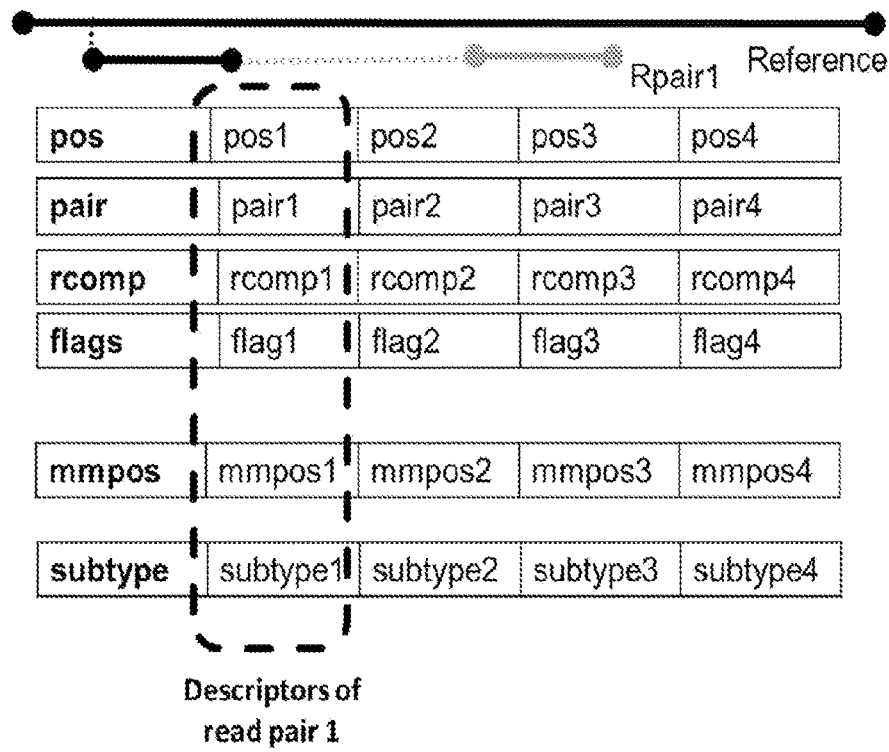
FIG. 14 shows the descriptors used to encode a pair of constant length reads mapping on the reference sequence with at least one substitution (Class M).
Figure 15:
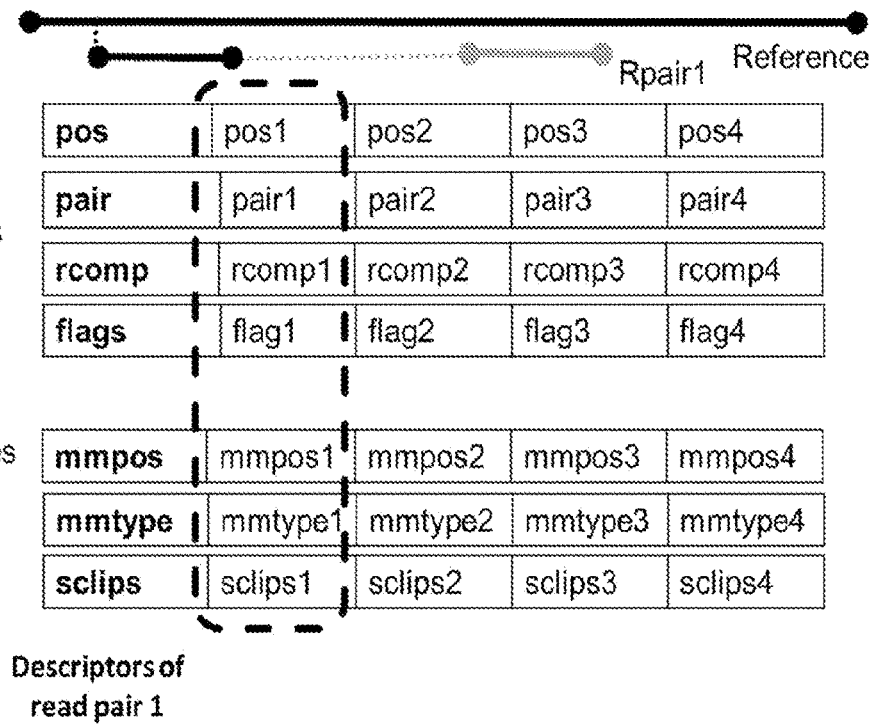
FIG. 15 shows the descriptors used to encode a pair of constant length reads mapping on the reference sequence with at least one insertion, deletion or soft clipped base (Class I).

An example of the encoding of a read pair of this type is provided in FIG. 14.

In this invention disclosure such read or read pair is said to belong to Class M.

Encoding Read or Read Pairs with at Least One Insertion, Deletion or Soft Clip

When a read or read pair maps on the reference sequence with at least one insertion deletion or soft clip, the following sub-set of descriptors is defined:

A position descriptor per read or read pair (pos)
A reverse complement descriptor per read or two per read pair (rcomp)
A descriptor per each position of mismatch (insertion, deletion, substitution) (mmpos)
A descriptor per each type of mismatch (insertion, deletion, substitution) (mmtype)
A descriptor per each sequence of soft clips (sclips)
A position per each unknown base (nmis)
A length descriptor per read (in case of variable length reads only) (rlen)
A pairing descriptor per read pair (pair)
A set of mapping flags (flags)

Descriptors already present in class M sub-set have the same syntax and semantics. The additional descriptors used in this case are mmpos to represent the position of substitutions, insertions and deletions, mmtype to represent the type of mismatch (substitutions, insertion or deletion) and sclips to represent the soft clipped bases.

In this invention disclosure such read or read pair is said to belong to Class I. An example of the encoding of a read pair belonging to Class I is provided in FIG. 15.

Read Pairs in which Only One Read is Mapped to a Reference Sequence

In the case a read pair is composed by a mapped read (belonging to any of the class P, N, M or I) and an unmapped read, the pair is classified as belonging to a separate class called Class HM (Half Mapped).

The read mapped to the reference sequence can be of any of the classes described above (P, N, M and I) and is encoded using the sub-set of descriptors already described for each class. The unmapped read is encoded by compressing the string of symbols representing it using an appropriate entropy coder.

Reference Sequences Descriptors

A reference sequence is commonly represented as a string of symbols representing the nucleotides that can be found in the corresponding biological sample. In the case of DNA the nucleotides are four and represented by the symbols A, C, G and T. In the case of RNA the T is replaced by U. A fifth symbol is added to denote a coordinate in the sequence where the sequencing device was not able to determine the type of nucleotides according to the confidence required by the experiment. In this disclosure a reference sequence can be encoded either entirely in one Access Unit or partitioned into two or more sub-sequences.

The descriptor used to represent reference sequences or sub-sequences to be entropy coded is the verbatim representation of the sequence or sub-sequence in terms of the allowed symbols of the respective alphabet.

Classification of the Sequence Reads According to Matching Rules

The sequence reads generated by sequencing machines are classified by the disclosed invention into six different "classes" according to the matching results of the alignment with respect to one or more "pre-existing" reference sequences.

When aligning a DNA sequence of nucleotides with respect to a reference sequence the following cases can be identified:

1. A region in the reference sequence is found to match the sequence read without any error (i.e. perfect mapping). Such sequence of nucleotides is referenced to as "perfectly matching read" or denoted as "Class P".

2. A region in the reference sequence is found to match the sequence read with a type and a number of mismatches determined only by the number of positions in which the sequencing machine generating the read was not able to call any base (or nucleotide). Such type of mismatches are denoted by an "N", the letter used to indicate an undefined nucleotide base. In this document this type of mismatch are referred to as "n type" mismatch. Such sequences belong to "Class N" reads. Once the read is classified to belong to "Class N" it is useful to limit the degree of matching inaccuracy to a given upper bound and set a boundary between what is considered a valid matching and what it is not. Therefore, the reads assigned to Class N are also constrained by setting a threshold (MAXN) that defines the maximum number of undefined bases (i.e. bases called as "N") that a read can contain. Such classification implicitly defines the required minimum matching accuracy (or maximum degree of mismatch) that all reads belonging to Class N share when referred to the corresponding reference sequence, which constitutes an useful criterion for applying selective data searches to the compressed data.

3. A region in the reference sequence is found to match the sequence read with types and number of mismatches determined by the number of positions in which the sequencing machine generating the read was not able to call any nucleotide base, if present (i.e. "n type" mismatches), plus the number of mismatches in which a different base, than the one present in the reference, has been called. Such type of mismatch denoted as "substitution" is also called Single Nucleotide Variation (SNV) or Single Nucleotide Polymorphism (SNP). In this document this type of mismatch is also referred to as "s type" mismatch. The sequence read is then referenced to as "M mismatching reads" and assigned to "Class M". Like in the case of "Class N", also for all reads belonging to "Class M" it is useful to limit the degree of matching inaccuracy to a given upper bound, and set a boundary between what is considered a valid matching and what it is not. Therefore, the reads assigned to Class M are also constrained by defining a set of thresholds, one for the number "n" of mismatches of "n type" (MAXN) if present, and another for the number of substitutions "s" (MAXS). A third constraint is a threshold defined by any function of both numbers "n" and "s", f(n,s). Such third constraint enables to generate classes with an upper bound of matching inaccuracy according to any meaningful selective access criterion. For instance, and not as a limitation, f(n,s) can be $(n+s)^{1/2}$ or $(n+s)$ or any linear or non-linear expression that sets a boundary to the maximum matching inaccuracy level that is admitted for a read belonging to "Class M". Such boundary constitutes a very useful criterion for applying the desired selective data searches to the compressed data when analyzing sequence reads for various purposes because it makes possible to set a further boundary to any possible combination of the number of "n type" mismatches and "s type" mismatches (substitutions) beyond the simple threshold applied to the one type or to the other.

4. A fourth class is constituted by sequencing reads presenting at least one mismatch of any type among "insertion", "deletion" (a.k.a. indels) and "clipped", plus, if present, any mismatches type belonging to class N or M. Such sequences are referred to as "I mismatching reads" and assigned to "Class I". Insertions are constituted by an additional sequence of one or more nucleotides not present in the reference, but present in the read sequence. In this document this type of mismatch is referred to as "i type" mismatch. In literature when the inserted sequence is at the edges of the sequence it is also referred to as "soft clipped" (i.e. the nucleotides are not matching the reference but are kept in the aligned reads contrarily to "hard clipped" nucleotides which are discarded). In this document this type of mismatch is referred to as "c type" mismatch. Keeping or discarding nucleotides is a decisions taken by the aligner stage and not by the classifier of reads disclosed in this invention which receives and processes the reads as they are determined by the sequencing machine or by the following alignment stage. Deletion are "holes" (missing nucleotides) in the read with respect to the reference. In this document this type of mismatch is referred to as "d type" mismatch. Like in the case of classes "N" and "M" it is possible and appropriate to define a limit to the matching inaccuracy. The definition of the set of constraints for "Class I" is based on the same principles used for "Class M" and is reported in Table 1 in the last table lines. Beside a threshold for each type of mismatch admissible for Class I data, a further constraint is defined by a threshold determined by any function of the number of the mismatches "n", "s", "d", "i" and "c", $w(n,s,d,i,c)$. Such additional constraint make possible to generate classes with an upper bound of matching inaccuracy according to any meaningful user defined selective access criterion. For instance, and not as a limitation, $w(n,s,d,i,c)$ can be $(n+s+d+i+c)^{1/5}$ or $(n+s+d+i+c)$ or any linear or non-linear expression that sets a boundary to the maximum matching inaccuracy level that is admitted for a read belonging to "Class I". Such boundary constitutes a very useful criterion for applying the desired selective data searches to the compressed data when analyzing sequence reads for various purposes because it enables to set a further boundary to any possible combination of the number of mismatches admissible in "Class I" reads beyond the simple threshold applied to each type of admissible mismatch.

5. A fifth class includes all reads that do not find any mapping considered valid (i.e not satisfying the set of matching rules defining an upper bound to the maximum matching inaccuracy as specified in Table 1) for each data class when referring to the reference sequence. Such sequences are said to be "Unmapped" when referring to the reference sequences and are classified as belonging to the "Class U".

Classification of Read Pairs According to Matching Rules

The classification specified in the previous section concerns single sequence reads. In the case of sequencing technologies that generates read in pairs (i.e. Illumina Inc.) in which two reads are known to be separated by an unknown sequence of variable length, it is appropriate to consider the classification of the entire pair to a single data class. A read that is coupled with another is said to be its "mate".

If both paired reads belong to the same class the assignment to a class of the entire pair is obvious: the entire pair is assigned to the same class for any class (i.e. P, N, M, I, U). In the case the two reads belong to a different class, but none of them belongs to the "Class U", then the entire pair is assigned to the class with the highest priority defined according to the following expression:

$$P<N<M<I$$

in which "Class P" has the lowest priority and "Class I" has the highest priority.

In case only one of the reads belongs to "Class U" and its mate to any of the Classes P, N, M, I a sixth class is defined as "Class HM" which stands for "Half Mapped".

Figure 20:
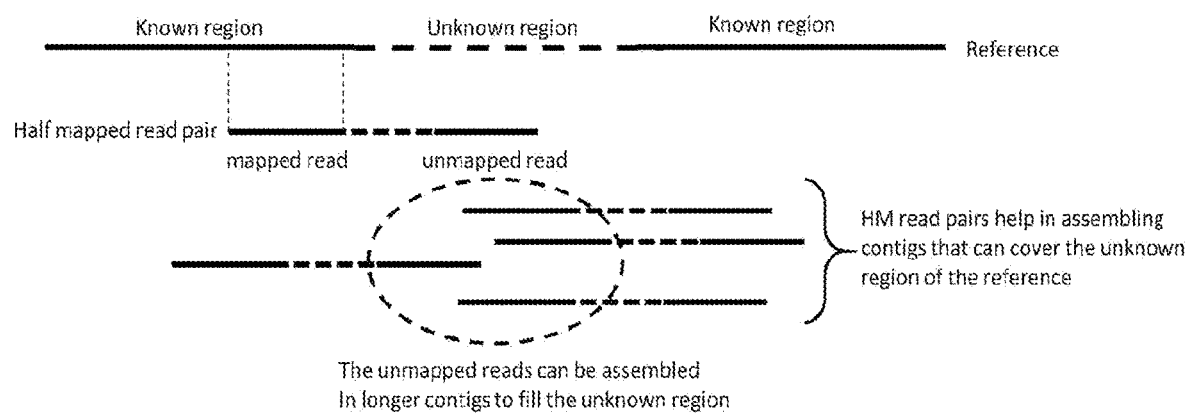
FIG. 20 shows how half mapped read pairs (Class HM) can be used to fill unknown regions of a reference sequence by assembling longer sequences (a.k.a. "contigs") with unmapped reads.

The definition of such specific class of reads is motivated by the fact that it is used for attempting to determine gaps or unknown regions existing in reference genomes (a.k.a. little known or unknown regions). Such regions are reconstructed by mapping pairs at the edges using the pair read that can be mapped on the known regions. The unmapped mate is then used to build the so called "contigs" of the unknown region as it is shown in FIG. 20. Therefore providing a selective access to only such type of read pairs greatly reduces the associated computation burden enabling much efficient processing of such data originated by large amounts of data sets that using the state of the art solutions would require to be entirely inspected.

The table below summarizes the matching rules applied to reads in order to define the class of data each read belongs to. The rules are defined in the first five columns of the table in terms of presence or absence of type of mismatches (n, s, d, i and c type mismatches). The sixth column provide rules in terms of maximum threshold for each mismatch type and any function $f(n,s)$ and $w(n,s,d,i,c)$ of the possible mismatch types.

TABLE 3

Type of mismatches and set of constrains that each sequence reads must satisfy to be classified in the data classes defined in this invention disclosure.

| Number and types of mismatches found when matching a read with a reference sequence | | | | | | |
|---|---|---|---|---|---|---|
| Number of unknown bases ("N") | Number of substitutions | Number of deletions | Number of Insertions | Number of clipped bases | Set of matching accuracy constraints | Assignment Class |
| 0 | 0 | 0 | 0 | 0 | 0 | P |
| n > 0 | 0 | 0 | 0 | 0 | n ≤ MAXN | N |
|  |  |  |  |  | n > MAXN | U |
| n ≥ 0 | s > 0 | 0 | 0 | 0 | n ≤ MAXN and s ≤ MAXS and f(n, s) ≤ MAXM | M |

TABLE 3-continued

Type of mismatches and set of constrains that each sequence reads must satisfy to be classified in the data classes defined in this invention disclosure.

| Number and types of mismatches found when matching a read with a reference sequence | | | | | | |
|---|---|---|---|---|---|---|
| Number of unknown bases ("N") | Number of substitutions | Number of deletions | Number of Insertions | Number of clipped bases | Set of matching accuracy constraints | Assignment Class |
| | | | | | n > MAXN or s > MAXS or f(n, s) > MAXM | U |
| n ≥ 0 | s ≥ 0 | d ≥ 0* *At least one mismatch of type d, i, c must be present (i.e. d > 0 or i > 0 or c > 0) | i ≥ 0* | c ≥ 0* | n ≤ MAXN and s ≤ MAXS and d ≤ MAXD and i ≤ MAXI and c ≤ MAXC w(n, s, d, i, c) ≤ MAXTOT | I |
| | | d ≥ 0 | i ≥ 0 | c ≥ 0 | n > MAXN or s > MAXS or d > MAXD or i > MAXI or c > MAXC w(n, s, d, i, c) > MAXTOT | U |

Summary of Definitions

TABLE 4

Summary of Definitions of elements and features associated to Access Units.

| | |
|---|---|
| Reference Sequence | Sequence of nucleotides associated to a monodimensional integer coordinate system for which each integer coordinate is associated to a single nucleotide. Coordinate values can only be equal or larger than zero. This coordinate system in the context of this disclosure is zero-based (i.e. the first nucleotide has coordinate 0 and is said to be at position 0) and linearly increasing from left to right. |
| Base | In the context of this disclosure "base" is used as synonymous of "nucleotide". |
| Genomic Segment | Contiguous sequence or sub-sequence of bases |
| Base Position | The number of bases between a base and the left-most mapped base belonging to the same Genomic Segment. |
| Genomic Record | Data structure encoding either a single sequence read or a paired sequence read optionally associated with alignment information, read identifier and quality values. |
| Genomic Record Length | Distance between the left-most mapped base coded in the record and the right-most mapped base coded in the record. |
| Genomic Range | Interval of positions on a reference sequence defined by a start position s and an end position e such that s ≤ e. The start and end position of a Genomic Range are always included in the Range. |
| Genomic Record Position | Position of the left-most mapped base of the Genomic Record on the Reference Sequence. Mapped bases in a Genomic Record include: a base of the aligned read matching the corresponding base on the Reference Sequence a base of the aligned read that does not match the corresponding base (a.k.a. Single Nucleotide Polymorphism) A base present in the aligned read and not present in the Reference Sequence (a.k.a. insertion) and bases preserved by the alignment process, but not mapped on the Reference Sequence (a.k.a. soft clips) do not have mapping positions. |
| Access Unit | Logical data structure containing a coded representation of genomic information or related metadata to facilitate the bit stream access and manipulation. It is the smallest data organization that can be decoded by a decoder. According to the type of coded information, an AU can be decoded either independently of any other AU or using information contained in other AUs. AU can be of several types according to the nature of the coded data. |
| AU Type 0 | AUs containing a coded representation of a Reference Genome or part thereof. They can be decoded independently of any other AU. |
| AU Type 1 | AUs containing a coded representation of genomic sequence reads belonging to Class P data optionally associated to Read Names and Quality Values. Type 1 AU can either be decoded independently of any other AU or require one or more Type 0 AU according to the encoding strategy. |

TABLE 4-continued

Summary of Definitions of elements and features associated to Access Units.

| | |
|---|---|
| AU Type 2 | AUs containing a coded representation of genomic sequence reads belonging to Class N data optionally associated to Read Names and Quality Values. Type 2 AU can either be decoded independently of any other AU or require one or more Type 0 AU according to the encoding strategy. |
| AU Type 3 | AUs containing a coded representation of genomic sequence reads belonging to Class M data optionally associated to Read Names and Quality Values. Type 3 AU can either be decoded independently of any other AU or require one or more Type 0 AU according to the encoding strategy. |
| AU Type 4 | AUs containing a coded representation of genomic sequence reads belonging to Class I data optionally associated to Read Names and Quality Values. Type 4 AU can either be decoded independently of any other AU or require one or more Type 0 AU according to the encoding strategy. |
| AU Type 5 | AUs containing a coded representation of genomic sequence reads belonging to Class HM data optionally associated to Read Names and Quality Values. Type 5 AU can either be decoded independently of any other AU or require one or more Type 0 AU according to the encoding strategy. |
| AU Type 6 | AUs containing a coded representation of genomic sequence reads belonging to Class U data optionally associated to Read Names and Quality Values. Type 6 AU can always be decoded independently of any other AU. |
| Access Unit Start Position | Left-most Genomic Record Position among all Genomic Records contained in the Access Unit. |
| Access Unit End Position | Right-most base position among all mapped bases of all Genomic Records contained in the Access Unit |
| Access Unit Range | Genomic Range comprised between the AU Start Position and the right-most Genomic Record Position among all Genomic Records contained in the Access Unit |
| Access Unit Size | Number of Genomic Records contained in an Access Unit |
| Access Unit Covered Region | Genomic Range comprised between the AU Start Position and the AU End Position |

Partitioning of Compressed Descriptors Sub-Sets into Access Units and Modes for Storing Access Units into File Systems or Streaming to a Client Once reads or reads pairs are classified and coded into genomic records by the appropriate sub-sets of descriptors, the streams of entropy coded descriptors are partitioned into Access Units characterized by their relative Access Unit Range. In other words Access Units collects only genomic records that map their left-most base inside the Access Unit Range associated to each Access Unit. The definition of Access Units Ranges for a genomic dataset can be of two types: non-overlapping or overlapping.

When Access Units are stored into file systems two useful modes for mapping Access Units on the physical storage media can be defined and implemented:

a) the Access Unit Contiguous (AUC) mode, in which block of data from different Descriptors Streams, but belonging to the same Access Unit, are stored contiguously.

b) the Descriptor Stream Contiguous (DSC) mode, in which data blocks belonging to the same descriptors, but belonging to different Access Units are stored in contiguous regions of the file system The AUC mode is of particular interest for the minimization of file system accesses in case of genomic region based selective access, as it enables storing data belonging to the same Access Unit in contiguous areas of the storage device.

The DSC mode implements a different data organization grouping all data blocks belonging to the same descriptors in contiguous areas of the storage device. For this reason, the DSC mode result interesting and efficient for other use cases than genomic region based selective access, such as for instance when only one or any sub-set of Descriptors Streams need to be encrypted, in which case the data contiguity of descriptors of the same type makes the operation more efficient.

Figure 16:
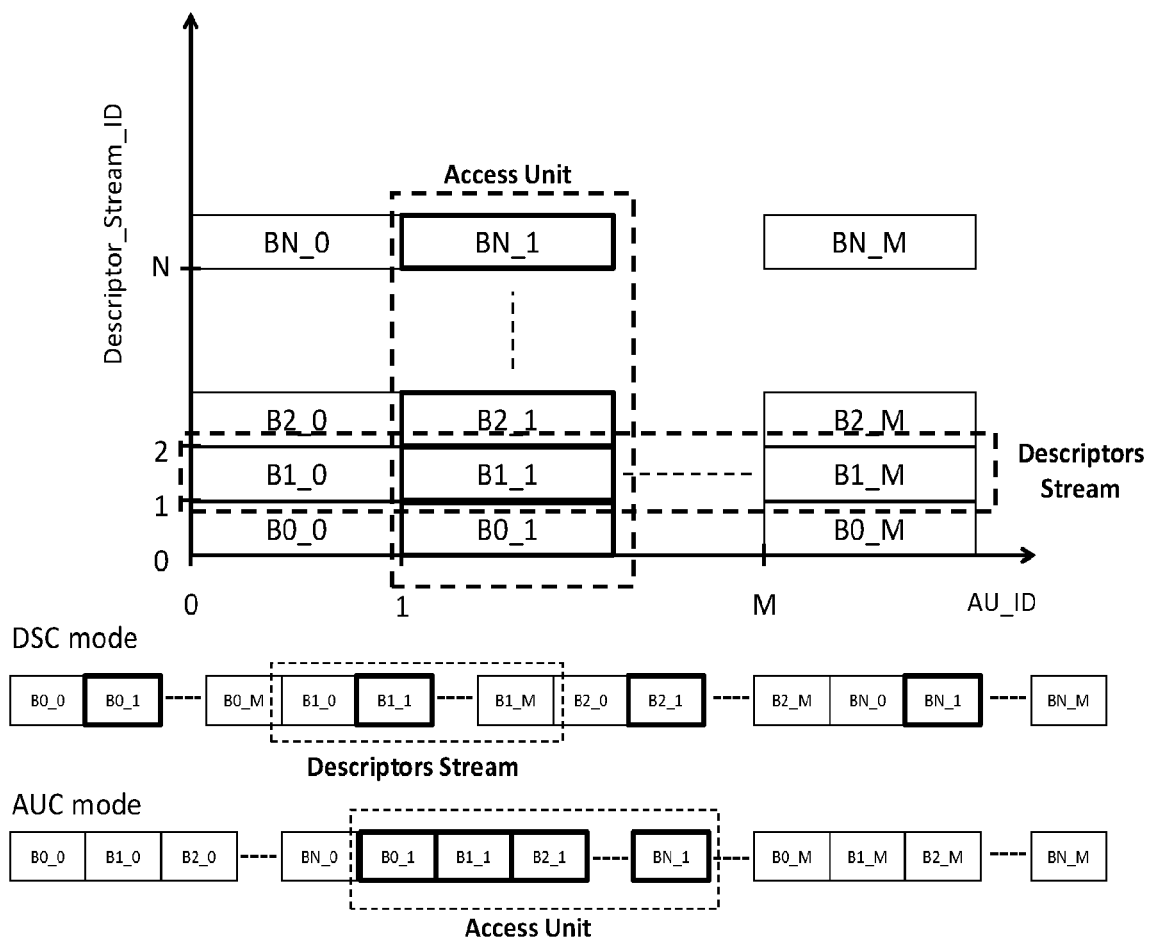
FIG. 16 shows the two ways of storing Access Units of the same class of data on a filesystem. Using the DSC mode the block of data of the same descriptor stream belonging to the different access units are stored contiguously. Using the AUC mode the data blocks of different descriptor streams, but belonging to the same Access Unit are stored contiguously. On the vertical axis are reported the different descriptors streams identified by a specific identifier (Descriptor_Stream_ID), on the horizontal axis the different Access Units as ordered in the Master Index Table, and identified by an index within each descriptor stream and data class, for both overlapping and non-overlapping cases.

An illustration of the data mapping configurations defined for the AUC and the DSC storage mapping modes is reported in FIG. 16.

Furthermore the AUC mode cam be implemented in two different ways in terms of AU ordering on the storage media. The order of Access Units in the storage device can be either class-based, with all Access Units of the same data class stored in the same area of the storage device (Class Contiguous mode CC), or genomic region based, with all Access Units mapping to the same or closest genomic region stored in the same area of the storage device (Genomic Region Contiguous mode GRC). The AUC/CC mode results more efficient when only accessing data of a single class, the AUC/GRC mode result more efficient when accessing data of different classes mapping to the same genomic region. An illustration of the data mapping configuration defined by the CC and GRC storage mapping modes is reported in FIG. 17.

In the case of streaming AUs to a client by means of transport packets carrying segments of an AU, obviously only the AUC mode can be employed.

The information characterizing the genomic region associated to the data contained into the Access Units (i.e. the Access Unit Range and Access Unit is stored and is available into a multidimensional data structure called Master Index Table that is structured and contains the following information:

1. The position, as number of nucleotides, of the left-most matching base among all reads or read pairs contained in the Access Unit, with regards to the reference sequence.
2. The position, as number of nucleotides, of the right-most matching base among all reads or read pairs contained in the Access Unit, with regards to the reference sequence.
3. The lists of access unit sizes (when the AUC mode is used).
4. The list of offsets, expressed as number of bytes, of the first byte of each descriptor data block of each Access Unit, with respect to the first byte of the Dataset payload.

The information on the way data is partitioned into Access Units and how Access Units are stored into the file system is necessary to be able to optimize the data access process. This is the reason for which such information is registered into the Dataset Header and made available when selective data access is performed by a decoding unit.

Technical Advantages of the AUC Versus the DSC Mode

TABLE 5

Technical advantages of the DSC versus the AUC mode.

| Contiguity Mode | Technical Advantages |
|---|---|
| DSC | Processing of Descriptor Streams such as encryption/decryption, analysis of descriptor values and statistics is more efficient because relevant data are contiguous in file system.<br>No overhead is introduced by the presence of Block Headers. |
| AUC | Selective access is easier as Access Units are stored contiguously in file: no need to jump to sparse locations of the file system when accessing Blocks composing the same Access Unit. |

Optimization of Genomic Region Based Selective Data Access

Selective access to a specific genomic region is performed by: 1) identifying the Access Units covering the specified region on the reference sequence and 2) accessing the appropriate data. The next sections describe how knowing the storage mode used (AUC or DSC) the access to data for the AU identified as answering the selective data access request can be optimized.

Data Access when AU are Stored Using the DSC Mode

With reference to FIG. 16, when accessing Access Unit M, composed by Blocks B_0_M to B_N_M, the Block_Byte_Offset[Sequence_ID][Class_ID][M][0] entry of the Master Index Table is used to seek to the first byte of the Access Unit:

1) fseek(FILE, Block_Byte_Offset[Sequence_ID][Class_ID][M][0], Dataset_Payload_First_Byte_Offset)

Then a difference between Block_Byte_Offset[Sequence_ID][Class_ID][M+1][0] and Block_Byte_Offset[Sequence_ID][Class_ID][M][0] is calculated in order to know the size of the Block and read its payload accordingly:

2) fread(payload_buffer, Block_Byte_Offset[Sequence_ID][Class_ID][M+1][0]−Block_Byte_Offset[Sequence_ID][Class_ID][M][0], 1, FILE)

Steps 1 and 2 are repeated for all Blocks in the Access Unit, until the last one with index N=Num_Descriptors[Sequence_ID][Class_ID]−1:

2×N+1) fseek(FILE, Block_Byte_Offset[Sequence_ID][Class_ID][M][N], Dataset_Payload_First_Byte_Offset)

2×N+2) fread(payload_buffer, Block_Byte_Offset[Sequence_ID][Class_ID][M+1][N+1]−Block_Byte_Offset[Sequence_ID][Class_ID][M][N], 1, FILE)

Data Access when AU are Stored Using the AUC Mode

With reference to FIG. 16, when accessing Access Unit M, composed by Blocks B_0_M to B_N_M, the Block_Byte_Offset[Sequence_ID][Class_ID][M][0] entry of the Master Index Table is used to seek to the first byte of the Access Unit:

1) fseek(FILE, Block_Byte_Offset[Sequence_ID][Class_ID][M][0], Dataset_Payload_First_Byte_Offset)

Then the AU_Size[Sequence_ID][Class_ID][M] entry of the Master Index Table is used to read the Access Unit as a monolithic chunk of data:

2) fread(payload_buffer, AU_Size[Sequence_ID][Class_ID][M], 1, FILE)

Comparison of Data Access Efficiency for the AUC and DSC Modes for Genome Region Based Selective Access Retrieving data belonging to an AU identified as covering a specific genomic region relevant for the selective access request is more efficient when the AUC mode is used since only one seek and one read, meaning that the number of accesses to disk per AU is largely minimized, compared to the 2×N+2 seek+read operations necessary in DSC mode. Physical storage devices have in general relatively high seek time compared to their throughput. In other words, they take relatively long to start reading, but once started, they can read consecutive bytes relatively fast. That is why it is always preferable to minimize seeks and prefer monolithic reads.

The information about the guarantee that the AUC mode is employed available in the Dataset Header is necessary to be able to implement efficient monolithic reads.

Optimization of Descriptor Stream Selective Data Access

In some use cases such as performing separate accesses to only some descriptors or applying encryption/decryption to one or a sub-set of Descriptors Stream separately the DSC mode result much more efficient. Knowing that the DSC data storage mode in the file system is used by an appropriate signaling in the Dataset Header makes such processing of geneomic information much more efficient as described in the sections below.

Data Access when AU are Stored Using the DSC Mode

With reference to Table 7, when accessing Descriptors Stream N (Class_ID=C, Descriptor_ID=D), composed by Blocks B_N_0 to B_N_M, the Block_Byte_Offset[0][C][0][D] entry of the Master Index Table is used to seek to the first byte of the Descriptors Stream:

1) fseek(FILE, Block_Byte_Offset[0][C][0][D], Dataset_Payload_First_Byte_Offset)

Then the Descriptors_Stream_Size[C][D] entry of the Master Index Table is used to read the Descriptors_Stream as a monolithic chunk of data:

2) fread(payload_buffer, Descriptors_Stream_Size[C][D], 1, FILE)

Data access and or other processing operations such as encryption for instance, but not as limitation, are then performed on payload_buffer.

Data Access when AU are Stored Using the AUC Mode

With reference to Table 7, when accessing Descriptors Stream N (Class_ID=C, Descriptor_ID=D), composed by Blocks B_N_0 to B_N_M, the Block_Byte_Offset[0][C][0][D] entry of the Master Index Table is used to seek to the first byte of the Descriptors Stream:

1) fseek(FILE, Block_Byte_Offset[0][C][0][D], Dataset_Payload_First_Byte_Offset)

Then the Block_Header of the Block is read:

2) fread(header_buffer, Block_Header_Size, 1, FILE)

Then the BS field of the Block_Header is used to read the Block payload:

3) fread(payload_buffer[0], BS, 1, FILE)

Steps 1 to 3 are repeated for all Blocks (N) composing the Descriptors Stream:

3×N+0) fseek(FILE, Block_Byte_Offset[Seq_Count][C][N][D], Dataset_Payload_First_Byte_Offset)

3×N+1) fread(header_buffer, Block_Header_Size, 1, FILE)

3×N+2) fread(payload_buffer[N], BS, 1, FILE)

Comparison of Data Access Efficiency for the AUC and DSC Modes for Descriptor Stream Based Selective Access Descriptors Stream access and processing is more efficient by using the DSC mode as only two accesses to the storage device per Descriptors_Stream are needed, compared to 3×N+2 accesses in the AUC mode.

The implementation of an optimized (minimal) number of storage accesses is possible if the information that the DSC mode is usage for storing the data is available in the Dataset Header.

Once at data retrieval and decoding side, which partitioning of data into Access Units is implemented (overlapping or non-overlapping) and which mapping mode on the storage media is used DSC, AUC/CC or AUC/GRC to optimize the selective access process is then only necessary to identify which Access Units need to be decoded to have the guarantee that all reads mapping to the selected genomic regions are recovered. The information on the Access Unit Ranges and Access Units covered regions, as well as the threshold that determines when paired reads are coded as single entities or split into single reads is available respectively in the Master Index Table, in the Dataset Header. Such information is processed as detailed in the following section.

Read Pairs and Selective Access

The coded representation of read pairs as single entity is characterized by representing the "pairing distance" as coordinate difference of the mapping positions on the reference of the two reads composing the pair. Such descriptor can assume—in principle—any possible value between zero and any number up to the size of the entire reference sequence (e. g. almost 250 million bases for a human chromosome 1). Such possibility makes the selective access to aligned sequence data belonging only to specific genomic regions computationally expansive in terms of both data volume access and processing when it is required to guarantee that all reads belonging to such specific regions are correctly decoded with all the associated information and provided as result of the data access request. The problem is even more difficult to be solved and it requires much more bandwidth and processing resource when two reads in a pair are mapped on two different reference sequences.

The next sections describe how this invention disclosure solves the problem of selectively accessing genomic sequence read pairs encoded using descriptors grouped into independent Access Units.

Selective Access to Aligned Sequence Reads

Selective access to genomic data mapped to one or more reference sequences is usually performed by specifying the first (start) and last (end) coordinate of the selected genomic regions of the reference sequences (e.g. chromosomes).

When selective access is performed to retrieve reads or read pairs mapped on a genomic region defined by a start coordinate and an end coordinate, two behaviors of the retrieving and decoding process are considered as useful solutions to the problem:

1 the decoder retrieves entire genomic reads or only the genomic segments (down to a single base) overlapping the specified genomic region. The retrieving operation includes entire reads (when entirely contained in the specified genomic regions) or only the read portions mapping on the specified genomic region.

2 the decoder returns all reads or read pairs having at least one base mapped on the specified genomic region.

Figure 10:
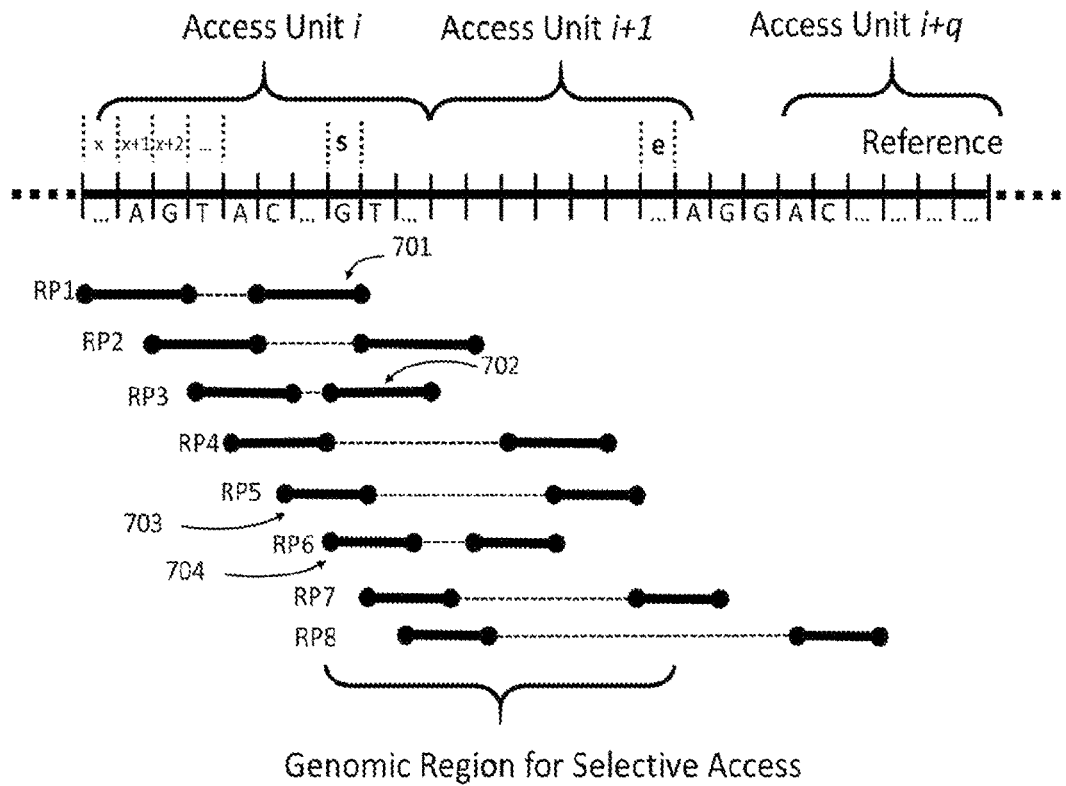
FIG. 10 shows how, according to the specific selective access behavior, reads 701, 702, 703 and 704 are returned either partially or entirely. In both cases Access Units K and K+1 shall be decoded.

FIG. 10 shows that in case of a decoding behavior as described in item 1, reads 701, 702, 703 and 704 would be returned only partially (those segments overlapping the specified genomic region), whereas in case of a retrieving and decoding behavior as described in item 2 they would be returned entirely. In both behavior cases to obtain the desired result, Access Units i and i+1 shall be decoded.

Case 1 and 2 differ only by the amount of data returned by the decoding application, but they share the need to determine which Access Units need to be decoded to provide the desired access to the data corresponding to the specified genomic region. This invention defines a new algorithm able to support both behavior cases itemized at point 1 and 2 and at the same time minimizing the number of Access Units that need to be decoded and inspected, which is equivalent to minimize the necessary data access bandwidth and processing (i.e. decoding) complexity. The identification of the Access Units that need to be decoded can be done only accessing the information available in the Dataset Header and parsing, even partially in some specific cases, the Master Index Table, all information easily accessible in the compressed domain.

Selective Access to Sequence Data Compressed into Access Units

Figure 7:
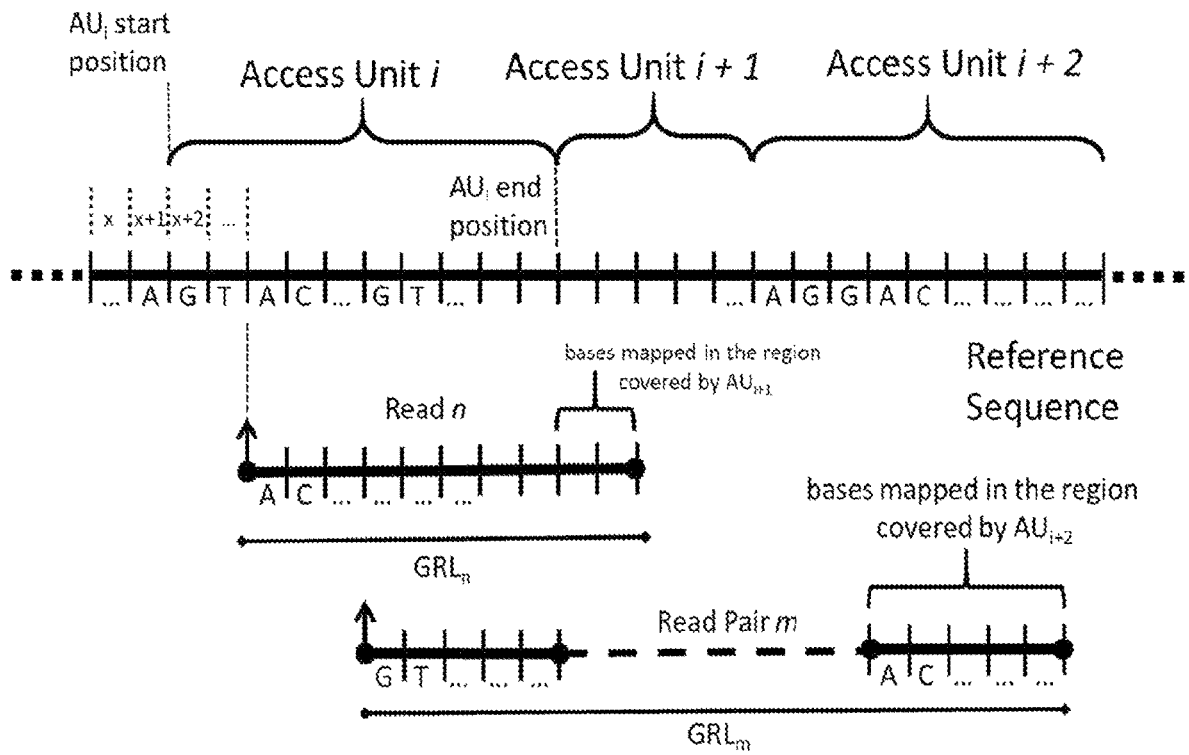
FIG. 7 shows how aligned reads or read pairs can span two or more Access Units. This happens when the respective genomic record length is larger than the distance of the read or read pair mapping position from the end of the AU containing the records. A consistent selective access algorithm shall be able to retrieve all bases overlapping the specified genomic region even if the read is encoded in an Access Units not covering the specified genomic region.

When the genomic data is compressed into Access Units and each Access Unit covers a specific genomic region, some reads can result to be mapped across the edges of the Access Unit range with part of the read mapped at genomic positions belonging to one Access Unit range and the other part of the read on the genomic region belonging to a preceding or following Access Unit (respectively in terms of smaller or larger coordinates on the reference sequence for the Access Unit Range boundaries). The occurrence of this possibility is clearly illustrated in FIG. 7.

The presence of reads pairs, as in the very common case of Illumina sequencing technology, poses an even greater challenge to the implementation of a consistent and efficient selective data access mechanism. This is due to the fact that to ensure compression efficiency the information that represents each read pair as single entity, can only be encoded in a single Access Unit that only covers a specific genomic region. So when it is required to access all read pairs that are mapped on a given genomic region, it is not sufficient to decode all Access Units that covers such region, but in principle it is necessary to decode and inspect all preceding Access Units to check if any Read 2 of a pair may be mapped in the genomic region for which the selective access is required. As can be easily be understood by a person skilled in the art, such procedure jeopardize all advantages in terms of bandwidth and processing complexity reductions that a selective access of compressed sequence data stored in Access Units covering specific genomic regions may and should offer.

In summary, the obstacle of achieving an efficient selective access procedure to read pairs represented as single entities (for high compression performance), and contained in compressed form in Access Units covering specific genomic regions, results particularly difficult because:

1. read pairs mapped near the edges of the Access Unit ranges may have portions or entire reads that are mapped outside the Access Unit range
2. the distance between a read and its mate may be large and the Read 2 can result to be mapped on a region covered by other Access Units, but is coded as single entity in the Access Unit in which Read 1 is coded.

This two possibilities are illustrated in FIG. 8 in which all read pairs are encoded in AU 1, but some segments of the pairs map genomic regions that are covered by other Access Units.

The efficient solution of the selective access problem provided in this disclosure solves both cases 1 and 2, is based on defining a specific coding and decoding technology that guarantees to access all reads mapping to the desired genomic region and at the same time provides the possibility of determining the minimum number of Access Units that need to be decoded. Such optimization constraint is equivalent to access and decode the minimal volume of data associated to the genomic region to be retrieved for any given partitioning of data into overlapping or non-overlapping Access Unit Ranges.

When read pairs are compressed by using a single data structure, and such coding approach is combined with the Access Units partitioning approach described in this disclosure the following cases may occur (see FIG. 8):

- part of a read in an Access Unit having range that only partially overlaps the genomic region said read is mapped to (201). This is true as well in case of single reads, but the problem occurs more often when dealing with paired-end reads whose average distance is usually much larger than the average read length
- a complete read in an Access Unit not covering the genomic region the read is mapped to (202 and 203)
- the combination of the two possibilities specified above (204)

An illustration of the three cases listed above is provided in FIG. 8 for different values of the pairing distance and read mapping positions. In the example of FIG. 8 read pairs RP2 and RP4 are mapped to a region entirely covered by Access Unit 1, whereas part of the nucleotides in pairs RP1, RP3 and RP5 map to positions covered by Access Unit 2 and RP6 has a mate that is far away from Access Unit 1 and 2.

Selective Access to Aligned Sequencing Reads Data and Access Units

A method for implementing an efficient selective access to reads or read pairs mapped on a reference sequence and coded in Access Units is described in the following sections. The method disclosed in this invention provides the advantage of determining and identifying a minimal number of Access Units to be decoded to have the guarantee that all single reads or read belonging to a pair mapping with at least one base on the genomic region Ron which the selective access is required.

In case the access to encoded (compressed) data belonging to a genomic region identified by the coordinate s and e on a reference sequence is required, the procedure disclosed in this invention identifies which are the Access Units that are necessary to be accessed and decoded to have the guarantee that all reads having at least one nucleotide mapped on the selected genomic region R for which the access is requested are retrieved.

Given any genomic region R of a reference sequence specified in terms of a start position s and an end position e, for a given set i of Access Units $AU_i$ and associated covered regions defined by a start coordinate $s_i$ and an end coordinate $e_i$, the minimum set of Access Units that needs to be accessed, decoded and inspected can be determined by identifying all Access Units $AU_i$ whose associated start coordinate $s_i$ or end coordinate $e_i$, satisfy one of the following expressions:

$s \leq s_i \leq e$

OR $s \leq e_i \leq e$

OR $s_i s$ AND $e_i \geq e$

Once the values of $s_i$ and $e_i$ are determined for each Access Unit during the encoding process, they can be stored either in an indexing data structure called Master Index Table for a storage scenario or in the header of each Transport Block in a streaming scenario. By inspecting the values of $s_i$ and $e_i$ contained in the Master Index Table or carried by each Transport Block header and comparing them with s and e determining the genomic region for which selective access is requested, it is possible to identify the minimum set of Access Units $AU_i$ that need to be accessed and decoded to satisfy the selective access request with the guarantee that all reads with at least one base mapped on the requested genomic regions are retrieved.

Decoding Process for Single Reads with Variable Length.

The following section describes the steps involved in selectively accessing a genomic region of compressed genomic data when the coded sequence reads have variable length.

1. An analyst or a genomic data processing application requires to access all encoded sequence data mapped to a genomic region defined by a coordinate s (start) on a reference sequence and a coordinate e (end) for which $s<e$.
2. The decoder accesses and decodes all Access Units $AU_i$ with $K \leq i \leq K+N$ ($AU_K$ to $AU_{K+N}$) for which:
   a. $s \in A_K$ (i.e. the start coordinate s belongs to the genomic region covered by $A_K$)
   b. $e \in A_{K+N}$ (i.e. the end coordinate e belongs to the genomic region covered by $A_{K+N}$)
   c.
3. The decoder has to determine how many Access Units $AU_i$ with $i<K$ have to be decoded in order to guarantee that all reads having at least one base mapped on the reference sequence at position $P \geq s$ are retrieved. The search selects for decoding all AUs for which $s \leq e_i \leq e$ and stops when all values of $e_i$ present in the MIT for the AU of the selected class have been parsed. Access Units having Start Position $s_i > e$ can be skipped since they do not contain any read having at least one base mapped in the genomic region selected for access.

Selective Access to Paired Reads

The new algorithm specified in this invention enables to implement a consistent and efficient selective access to sequence read and consist of the following steps:

1. The definition of a parameter MaxD that sets the threshold value for the pairing distance above which a read pair is encoded as two separate reads in separate Access Units and below which the reads are encoded in a single Genomic Record in the same Access Unit. Such mechanism prevents that reads that are mapped far away from their mate are encoded in an Access Units whose covered region would be far from the mapping coordinates (and therefore they would not be retrieved in case of selective access to the genomic region they cover).
2. The parameter MaxD, as set and used by the encoder to determine in which case pairs are coded as single entity, or coded as two separate reads, is stored in the "Dataset Header" of the file or transmitted in Transport Block Headers in streaming scenarios, so that MaxD is available at the decoder to perform the selective access process by decoding the minimum number of Access Units necessary to retrieve all reads of each pair mapped to the selected genomic region.

Given a genomic region of a reference sequence specified in terms of a start position s and an end position e, for a given set i of Access Units $AU_i$ and associated covered regions defined by a start coordinate $s_i$ and an end coordinate $e_i$, the minimum set of Access Units that need to be accessed, decoded and inspected can be determined by: identifying all Access Units $AU_i$ whose associated start coordinate $s_i$ or end coordinate $e_i$, satisfy the following expression:

$$s-\text{Max}D \le s_i \le e$$

Figure 9:
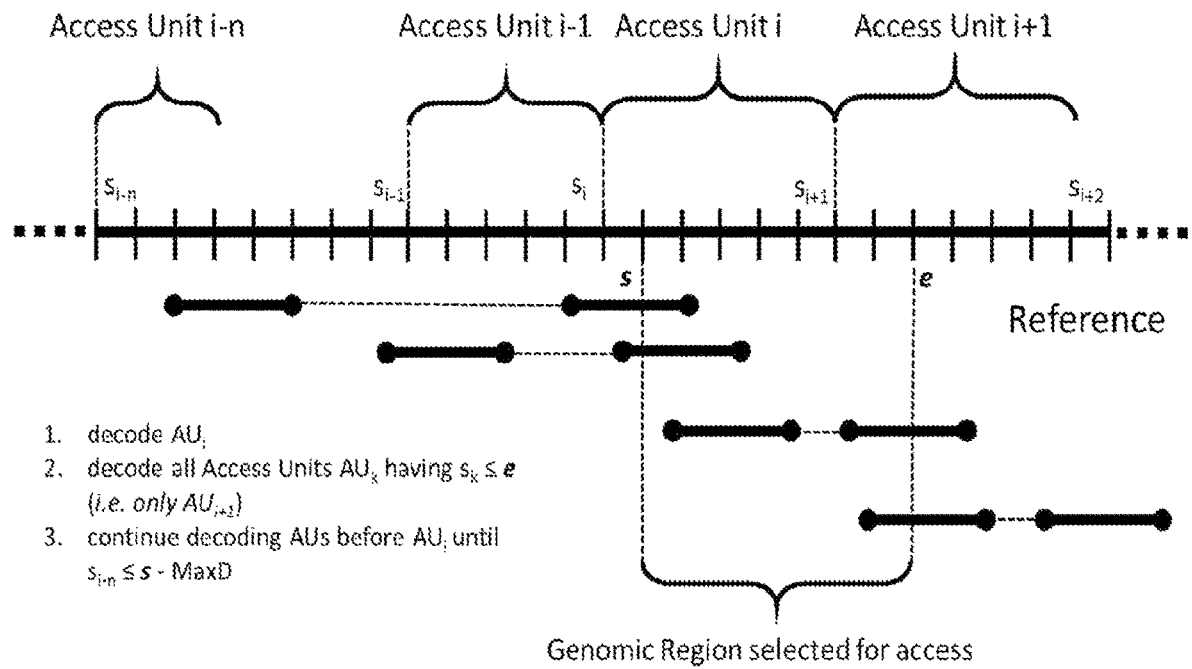
FIG. 9 shows an example of identification of AU and decoding process for the selective access to a region comprised between positions s and e in the case of read pairs and coding of pairs a single entity limited by a pairing distance threshold MaxD.

An example of determining $AU_i$ and identifying the corresponding Access Units is reported in FIG. 9. Once the values of $s_i$ and $e_i$ are determined for each Access Unit during the encoding process, they are stored in an indexing data structure called Master Index Table for a storage scenario. By inspecting the values of $s_i$ and $e_i$ contained in the Master Index Table and comparing them with s−MaxD and e determining the genomic region for which selective access is requested, it is possible to identify the minimum set of Access Units $AU_i$ that need to be accessed and decoded to satisfy the selective access request with the guarantee that all reads with at least one base mapped on the requested genomic regions are retrieved.

Decoding Process for Paired Reads with Constant Length.

The following text describes the steps involved in a selective access procedure to a genomic region of a reference sequence to which encoded genomic sequence read data with constant length maps to.

Figure 19:
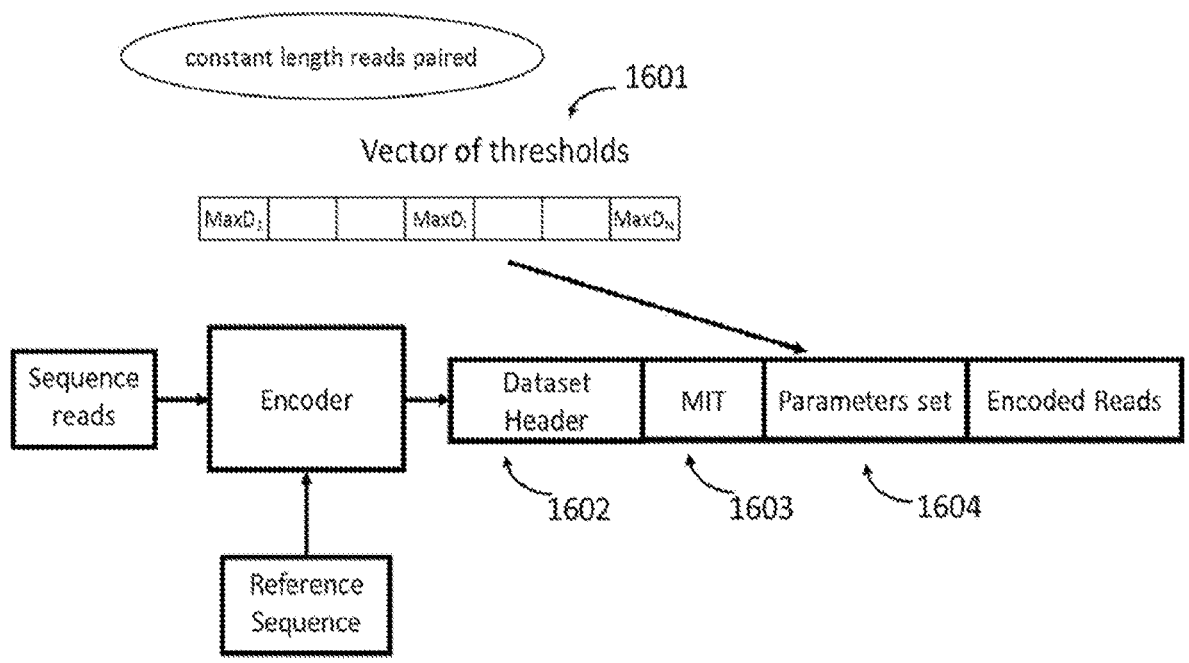
FIG. 19 shows an encoder associating to a compressed dataset the Dataset Header containing the information on the Access Unit partitioning mode used (overlapping or non-overlapping) and on the data storage format (DSC, AUC/CC, AUC/GRC) followed by the Master Index Table, the vector of encoding parameters used for each reference sequence to encode reads and read pairs and the encoded reads.

1. An analyst or a genomic data processing application requires to access all encoded genomic sequencing data mapped to a genomic region defined by a coordinate s (start) and a coordinate e (end) where s<e.
2. In order to find the AU containing coded reads having at least one base mapped in the specified interval, a decoding device implementing the selective access method described in this disclosure shall parse the MIT and:
   a. decode the $AU_K$ having the largest $s_K \le s$ and $e_K > s$
   b. decode all Access Units $AU_i$ with i>K having $s_i \le e$
   c. search for additional Access Units $AU_i$ having start position $s_i < s$ and end position $e_i > s$
   where $s_i$ and $e_i$ are the start position and end position of $AU_i$ The search described at point 2.c shall stop when $s_i < s-\text{Max}D$, where MaxD is the threshold for the pairing distance defined above to decide when a read pair has to be split and encoded in two distinct genomic records Scalar and Vector Parameters for MaxD The parameter MaxD described above can be a constant valid for the entire encoded genomic dataset or different values can be defined for different genomic regions. An appropriate approach is to define different parameter values per each reference sequence (e.g. chromosome). The reason why such approach may present technical advantages is that sequencing experiments may require that the density of generated sequence reads is different from one genomic region (e.g. chromosome) to another. In order to increase the compression efficiency, and at the same time maximize the efficiency of the selective access operation, it is appropriate to adapt the characteristic features of the selective access according to the density of the generated sequencing reads. Therefore, it is useful to use different values for the values of MaxD for each different reference sequence. So as to implement such selective access algorithm each encoded genomic dataset requires carrying a vector of MaxD values with each element of the vector associated to a different reference sequence. This is shown in FIG. 19 where a vector of thresholds (1601) is transported in the global Parameters Set container (1604) encoded by an encoding device implementing the method described in this disclosure.

Such approach has the additional advantage of being capable of supporting optimal parallel processing of encoded data where a different (cluster of) processing unit processes sequencing data mapped on a different reference sequence.

Dataset Header and Master Index Table

In order to support the indexing mechanism and selective access procedure described above two data structures are described here as integral part of the invention:

A Dataset Header (1602) carrying global parameters. The syntax of the Dataset Header is provided in Table 6.

An indexing tool called Master Index Table (MIT) is disclosed in this invention. The MIT syntax is provided in Table 4 related to mapped reads (i.e. reads classified as belonging to classes P, N, M, I or HM) is composed by two coordinates $Cs_{jk}$ and $Ce_{jk}$, expressing each Access Unit Start Position and End Position, where C denotes the read Class (i.e. $C \in \{P, N, M, I, HM\}$)

j denotes the reference sequence identifier k denotes the AU identifier within each reference sequence FIG. 18 shows an example of the Master Index Table defined above containing the Access Units Start Position ($Cs_k$) and End Position ($Ce_{jk}$).

The Master Index Table (1603) containing the coordinates defined above is encoded in a data structure together with the Dataset Header (1602) of the compressed genomic content as shown in FIG. 14. An example of such data structure is provided in Table 4.

| Syntax | Semantic |
| --- | --- |
| Dataset_Header { | |
|     Dataset_Group_ID | Identifier of Dataset Group ID |
|     Dataset_ID | Identifier of the Dataset. Its value shall be one of the IDs listed in the Datasets Group Header. |
|     Major_Brand | Brand identifier, identifying the data (compression) format specification the Dataset complies with. |
|     Minor_Version | Minor version number of the data (compression) format specification the Dataset complies with. |
|     Reads_Length | Length of reads in nucleotides. 0 in case of variable reads length. |
|     Paired_Reads | 1 if all reads in the Dataset are paired, 0 otherwise. |
|     Non_Overlapping_AU_Range | If set all AU of the dataset have non-overlapping ranges |

-continued

| Syntax | Semantic |
|---|---|
| Block_Header_Flag | If set, the AUC mode is enabled and all Blocks composing the Dataset are preceded by a Block Header. If not set the DSC mode is enabled. |
| CC_Mode_Flag | Used to signal the AU coding mode: AUC/CC or AUC/GRC. If set, two Access Units of one class cannot be separated by Access Units of a different class in the storage device. If unset, Access Units are ordered by Access Unit Start Position in the storage device. Not present if Block_Header_Flag is unset. |
| Alphabet_ID | A unique identifier for the type of alphabet used to encode mismatches of sequence reads with respect to the reference sequences. For example it is used to signal if DNA, RNA, IUPAC alphabets are used. |
| Seq_Count | Number of reference sequences used in this Dataset. |
| for (seq=0; seq<Seq_Count; seq++) { | |
|     Reference_ID[seq] | Unique identification number of the reference within this Dataset Group. |
|     Sequence_ID[seq] | Unambiguous identifier identifying the reference sequence(s) used in this Dataset. In common reference genomes such as GRCh37 these include at least the 24 chromosomes identifiers. |
| } | |
| for (seq=0;seq<Seq_Count;seq++) { | |
|     Seq_Blocks[seq] | Number of AUs per sequence. A value of 0 means not specified (e.g. in Transport Format). |
| } | |
| Dataset type | Type of genomic data coded in the dataset. For example "aligned", "not aligned". |
| Num_Classes | Number of classes encoded in the Dataset. |
| for (Class_ID =0;Class_ID<Num_Classes; Class_ID ++) { | |
|     Num_Descriptors[Class_ID] | Maximum number of Descriptors per Class encoded in the Dataset. |
| } | |
| U_clusters_num | Number of clusters of unmapped reads |
| U_signature_constant_length | 1 = constant length<br>0 = variable length |
| U_signature_size | Size in bits of the encoded signatures |
| if(U_signature_constant_length){ | |
|     U_signature_length | Length of clusters signature in nucleotides |
| } | |
| } | |

Dataset Header Syntax

The Dataset Header is a data structure carrying global parameters used by the encoder and the decoder to manipulate the encoded genomic information. The components and meaning of each element of the Dataset Header are listed in Table 4 below.

TABLE 6

Dataset Header.

| Syntax | Semantic |
|---|---|
| Dataset_Header { | |
|     Dataset_Group_ID | Identifier of Dataset Group ID |
|     Dataset_ID | Identifier of the Dataset. Its value shall be one of the IDs listed in the Datasets Group Header. |
|     Major_Brand | Brand identifier, identifying the data (compression) format specification the Dataset complies with. |
|     Minor_Version | Minor version number of the data (compression) format specification the Dataset complies with. |
|     Reads_Length | Length of reads in nucleotides. 0 in case of variable reads length. |
|     Paired_Reads | 1 if all reads in the Dataset are paired, 0 otherwise. |

TABLE 6-continued

Dataset Header.

| Syntax | Semantic |
|---|---|
| Non_Overlapping_AU_Range | If set all AU of the dataset have non-overlapping ranges |
| Block_Header_Flag | If set, the AUC mode is enabled and all Blocks composing the Dataset are preceded by a Block Header. If not set the DSC mode is enabled. |
| CC_Mode_Flag | Used to signal the AU coding mode: AUC/CC or AUC/GRC. If set, two Access Units of one class cannot be separated by Access Units of a different class in the storage device. If unset, Access Units are ordered by Access Unit Start Position in the storage device. Not present if Block_Header_Flag is unset. |
| Alphabet_ID | A unique identifier for the type of alphabet used to encode mismatches of sequence reads with respect to the reference sequences. For example it is used to signal if DNA, RNA, IUPAC alphabets are used. |
| Seq_Count | Number of reference sequences used in this Dataset. |
| for (seq=0; seq<Seq_Count; seq++) { | |
|     Reference_ID[seq] | Unique identification number of the reference within this Dataset Group. |
|     Sequence_ID[seq] | Unambiguous identifier identifying the reference sequence(s) used in this Dataset. In common reference genomes such as GRCh37 these include at least the 24 chromosomes identifiers. |
| } | |
| for (seq=0;seq<Seq_Count;seq++) { | |
|     Seq_Blocks[seq] | Number of AUs per sequence. A value of 0 means not specified (e.g. in Transport Format). |
| } | |
| Dataset type | Type of genomic data coded in the dataset. For example "aligned", "not aligned". |
| Num_Classes | Number of classes encoded in the Dataset. |
| for (Class_ID =1;Class_ID<Num_Classes; Class_ID ++) | |
| { | |
|     Num_Descriptors[Class_ID] | Maximum number of Descriptors per Class encoded in the Dataset. |
| } | |
| U_clusters_num | Number of clusters of unmapped reads |
| U_signature_constant_length | 1 = constant length<br>0 = variable length |
| U_signature_size | Size in bits of the encoded signatures |
| if(U_signature_constant_length){ | |
|     U_signature_length | Length of clusters signature in nucleotides |
|   } | |
| } | |

Master Index Table Syntax

An indexing tool called Master Index Table (MIT) is disclosed in this invention.

Table 5 provides the syntax for the Master Index Table defined in this disclosure where Class_ID is a unique identifier for the classes of mapped reads defined in this disclosure: P, N, M, I and HM classes. For example Class_ID could be defined as:

| Class_ID | 1 | 2 | 3 | 4 | 5 |
|---|---|---|---|---|---|
| Data class | P | N | M | I | HM |

The Master Index Table (MIT) is a data structure based on multi-dimensional array containing:

The position, as number of nucleotides, of the left-most matching base among the primary alignments of all reads or read pairs contained in the Access Unit, as a set of Blocks from different Descriptors Streams, with regards to the reference sequence. This is represented by Start_AU_Ref_Position[Sequence_ID][Class_ID][AU_ID] in Table 7.

The position, as number of nucleotides, of the right-most matching base among the primary alignments of all reads or read pairs contained in the Access Unit, as a set of Blocks from different Descriptors Streams, with regards to the reference sequence. This is represented by End_AU_Ref_Position[Sequence_ID][Class_ID][AU_ID] in Table 7.

The size of each Access Unit in bytes if each Access Unit is stored on the storage medium as a contiguous block of data, if each Access Unit is stored on the storage medium as a contiguous block of data The byte offset of the first byte of each coded Block of descriptors composing each AU of each class encoded with respect to each reference sequence. The offset is calculated with respect to the first byte of the Dataset Payload (0-based). If the Block is empty and (1)

Block_Header_Flag is set, it is equal to 0xFFFFFFFF. If the Block is empty and (2) Block_Header_Flag is unset, it is equal either to the Block_Byte_Offset value of the next block in the Descriptor Stream or, for the last Block in the Descriptor Stream, to the Descriptor Stream payload size. This is represented by Block_Byte_Offset[Sequence_ID][Class_ID][AU_ID][Descriptor_ID] in Table 7.

The alternative between the two coding methods is signaled by the flag called Block_Header_Flag in Table 7.

TABLE 7

Master Index Table.

| Syntax | Semantics |
|---|---|
| Master_Index_Table { | |
|   for (Sequence_ID=0;Sequence_ID<Seq_Count;Sequence_ID++) { | Sequence_ID is a unique identifier of a reference sequence and corresponds to the variable seq in the Dataset Header, as defined in Error! Reference source not found . . . Seq_Count is the total number of reference sequences and is encoded in the Dataset Header, as defined in Error! Reference source not found . . . |
|     for (Class_ID=0;Class_ID<Num_Classes;Class_ID++) { | Num_Classes is equal to field Num_Classes of Dataset Header, as defined in Error! Reference source not found . . . |
|       for (AU_ID=0;AU_ID<Seq_Blocks[Sequence_ID];AU_ID++) { | AU_ID is a unique identifier of the Access Unit. Seq_Blocks is an array of number of blocks per reference sequence and is encoded in the Dataset Header, as defined in Error! Reference source not found . . . |
|         Start_AU_Ref_Position[Sequence_ID][Class_ID][AU_ID] | The absolute position on the reference sequence identified by Sequence ID of the left-most mapped base among the primary alignments of all reads or read pairs contained in the AU and belonging to the class identified by Class_ID, in Access Unit identified by AU_ID. A reserved value is used if the Access Unit is empty. |
|         if (Block_Header_Flag) {<br>          AU_Size[Sequence_ID][Class_ID][AU_ID]<br>        }<br>        End_AU_Ref_Position[Sequence_ID][Class_ID][AU_ID] | The absolute position on the reference sequence identified by Sequence ID of the right-most mapped base among the primary alignments of all reads or read pairs contained in the AU and belonging to the class identified by Class_ID, in Access Unit identified by AU_ID. A reserved value is used if the Access Unit is empty. |
|         for (Descriptor_ID=0; Descriptor_ID < Num_Descriptors[Sequence_ID][Class_ID]; Descriptor_ID++) { | Num_Descriptors[Class_ID][Sequence_ID] is encoded in the Num_Descriptors field of the Dataset Header. Syntax of Num_Descriptors Dataset Header field is defined in Error! Reference source not found . . . |
|           Block_Byte_Offset[Sequence_ID][Class_ID][AU_ID][Descriptor_ID] | Byte offset of the first byte in the Block, with respect to the first byte of the Dataset Payload (0-based). If the |

TABLE 7-continued

Master Index Table.

| Syntax | Semantics |
|---|---|
| | Block is empty and (1) Block_Header_Flag is set it is equal to the reserved value signaling empty AU. If the Block is empty and (2) Block_Header_Flag is unset, it is equal either to the Block_Byte_Offset value of the next block in the Descriptor Stream or, for the last Block in the Descriptor Stream, to Descriptor_Stream_Size[Class_ID]. |
|           } <br>         } <br>       } <br>     } <br>     for (Cluster_ID=0;Cluster_ID<U_Clusters_num;Cluster_ID++) { <br>         for (AU_ID=0;AU_ID<Seq_Blocks[Sequence_ID];AU_ID++) { <br>             U_Cluster_Signature[Cluster_ID][AU_ID] <br>             for (Descriptor_ID=0; Descriptor_ID < Num_Descriptors[Sequence_ID][Class_ID]; Descriptor_ID++){ | |
| | Cluster signature |
|                 U_Cluster_Byte_Offset[Cluster_ID][AU_ID][Descriptor_ID] | Byte offset of the first byte in the Block, with respect to the first byte of the Dataset Payload (0-based). |
|             } <br>         } <br>     } <br> } | |

Transport Block Header Syntax

In Streaming scenarios the information carried by the Master Index table available in file systems or storage scenarios is carried by the Transport Block Header and associated to each data block belonging to any Access Units according to the following syntax.

TABLE 8

Transport Block Header syntax.

| Syntax | Key | Type | Semantic |
|---|---|---|---|
| Transport_Block_Header { | | | |
|   BSCP | | | Block Start Code Prefix. Identifies the beginning of a Block. Equal to 0x000001. |
|   Block_Header | | | Block_header as defined in Table 8 |
|   RF | | | Ref Flag. If RF is set, the Block contains both the SEQID field and the POS field. Shall be set in at least one Block of the Dataset. |
|   PF | | | Padding Flag. If PF is set, the Block contains additional padding bytes (after the payload) which are not part of the payload. |
|   AUID | | | Access Unit ID. Unambiguous ID, zero-based, linearly increasing by 1. It is encoded with respect to each reference (REFID), that it is reset when a new reference starts. Needed to enable random access. |
|   [Optional] REFID | | | Reference ID. Present if RF is set, otherwise it is inferred as equal to the last received REFID. Unambiguous ID, identifying the reference this Block refers to. |
|   [Optional] SEQID | | | Sequence ID. Present if RF is set, otherwise it is inferred as equal to the last received SEQID. Unambiguous ID, identifying the reference sequence this Block refers to. |
|   [Optional] Start_POS | | | Position of the left-most base of the first read in Block. Present if RF is set, otherwise it is inferred to be equal to the last received Start_POS. |

TABLE 8-continued

Transport Block Header syntax.

| Syntax | Key | Type | Semantic |
|---|---|---|---|
| [Optional] End_POS | | | Position of the right-most base of the last read in Block. Present if RF is set, otherwise it is inferred to be equal to the last received End_POS. |
| } | | | |

Block Header Syntax

TABLE 9

Block Header syntax.

| Syntax | Key | Type | Semantic |
|---|---|---|---|
| Block_Header { | | | |
| Descriptor_ID | | | Identifies the Descriptor. |
| Class_ID | | | Identifies the Class of data carried by the Block. |
| Block_size (BS) | | | Number of bytes composing the Block, including this header and the payload. |
| } | | | |

Transport Format to File Format Conversion Process

This section describes the process which enables the update of parameters Seq_Count and Seq_Blocks[seq] in the Dataset Header, defined above, and the compilation of the Master Index Table, defined in the previous section, from the syntax elements present in the Transport Block Header, described above.

Such a process is defined in order to guarantee that the resulting file retains in the Dataset Header and in the Master Index Table the equivalent information carried by the original Transport Format. Such a conversion process is used when it is required to store in a local storage device the data received via a Transport session, in order that the resulting file retains all information carried by a transport session and such information is formatted for appropriate file access.

The process is defined as follows:
1. Seq_Count is initialized to 0 and is incremented by 1 every time SEQID is different than any previously received SEQID.
2. Seq_Blocks[SEQID] is incremented by 1 every time the (SEQID, AUID) vector is different than any previous (SEQID, AUID) vector.
3. The coordinates of the Master Index Table, as defined in subclause 6.4.3.1, are calculated as follows:
   a. Sequence_ID=Seq_Count
   b. Class_ID=Class_ID in Block Header, defined in subclause 6.3.8.1
   c. AU_ID=Seq_Blocks[SEQID]
   d. If Block_Header_Flag is unset, Descriptor_ID=Descriptor_ID in Block Header, defined in subclause 6.3.8.1, else (Block_Header_Flag is set) Descriptor_ID=0.
4. The Master Index Table entry named Start_AU_Ref_Position[Sequence_ID][Class_ID][AU_ID] is calculated as follows:
   a. Start_AU_Ref_Position[Sequence_ID][Class_ID][AU_ID]=Start_POS
5. The Master Index Table entry named End_AU_Ref_Position[Sequence_ID][Class_ID][AU_ID] is calculated as follows:
   a. End_AU_Ref_Position[Sequence_ID][Class_ID][AU_ID]=End_POS
6. The Dataset Header field Block_Header_Flag is user defined.
7. If Block_Header_Flag is unset:
   a. Every time a Transport Block identified by a new (Class_ID, Descriptor_ID) vector is received, a new Descriptor Stream container (dscn), named DSCN[Class_ID][Descriptor_ID], is created and a variable named Block_Ptr[Class_ID][Descriptor_ID] is defined and initialized to 0.
   b. Block_Ptr[Class_ID][Descriptor_ID] is incremented by sizeof(gen_info)+Length of any gen_info child of DSCN[Class_ID][Descriptor_ID].
   c. The payload of all Blocks identified by Class_ID and Descriptor_ID in the Block Header is copied in the Value[ ] field of DSCN[Class_ID][Descriptor_ID].
   d. For each of the above Blocks, a new variable named Block_Ptr[Class_ID][Descriptor_ID][AU_ID] is defined and assigned the current value of Block_Ptr[Class_ID][Descriptor_ID].
   e. For each Block, Block_Ptr[Class_ID][Descriptor_ID] is incremented by Block_size−Transport_Block_Header_Size, where Transport_Block_Header_Size is the size in bytes of the Transport Block Header.
   f. Once the session is terminated and before writing the resulting data into the output file, a variable named DS_Offset is defined, initialized to 0.
   g. After writing each DSCN[Class_ID][Descriptor_ID] in the output file, DS_Offset is incremented by sizeof(gen_info header)+Length(DSCN[Class_ID][Descriptor_ID]).
   h. For each DSCN[Class_ID][Descriptor_ID] being written in the output file, the Master Index Table entry named Block_Byte_Offset[Sequence_ID][Class_ID][AU_ID][Descriptor_ID] is updated as follows:
   Block_Byte_Offset[Sequence_ID][Class_ID][AU_ID][Descriptor_ID]=DS_Offset+Block_Ptr[Class_ID][Descriptor_ID][AU_ID]

8. Else if Block_Header_Flag is set:
   a. A buffer named DatasetPayload is created.
   b. For each Block, the Block Header is extracted from the Transport Block Header and stored.
   c. Each Block, including the previously extracted Block Header and the Block payload, is written into DatasetPayload.
   d. For each Block, Block_Byte_Offset[Sequence_ID][Class_ID][AU_ID][Descriptor_ID] is equal to the byte offset of the Block in DatasetPayload.
   e. The Master Index Table entry named AU_Size[Sequence_ID][Class_ID][AU_ID] is calculated as the cumulated sum of (Block_size−Transport_Block_Header_Size) for each received Transport Block having the same Sequence_ID, Class_ID and AU_ID.
   f. At the end of the session, DatasetPayload is dumped into the output file as Dataset Payload, as defined in clause 5.4.

At the end of the process, typically when the end user stops the execution of the transport process, the third loop of the Master Index Table, i.e., for
(AU_ID=0; AU_ID<Seq_Blocks[Sequence_ID]; AU_ID++), must be re-ordered, per each combination of Sequence_ID and Class_ID indexes, by increasing value of
Start_AU_Ref_Position[Sequence_ID][Class_ID][AU_ID].

The invention claimed is:

1. A method for selectively accessing a genomic region in a file, said file being arranged into entropy coded Access Units $AU_i$, said method comprising the steps of:
   extracting values of start coordinate $s_i$ and end coordinate $e_i$ of said Access Units $AU_i$ from an indexing table contained in the file and disjointly coded from said $AU_i$ for the case of file stored information, and
   extracting a threshold value MaxD from the dataset header of said file, wherein said threshold value MaxD specifies the maximum value that the pairing distance of read pairs can assume, when read pairs are present in said file, such that said read pairs are coded as single entity or are separately coded.

2. The method of claim 1, wherein said indexing table contains the classes of Access Units in order to selectively identify the entropy coded Access Units according to the classes of data by employing a vector of pointers, without having to entropy decode said Access Units.

3. The method of claim 2, wherein said $AU_i$ comprise a range information named Access Unit range, said Access Unit range representing the genomic range comprised between the AU start position and the right most genomic record position of all genomic records contained in said AU.

4. The method of claim 3, wherein said AU can be of two different modes:
   a first mode in which blocks of data from different descriptors of the same AU are stored contiguously, and
   a second mode in which data blocks belonging to the same descriptors but belonging to different Access Units are stored in contiguous regions of the file.

5. The method of claim 4, wherein said mode information is coded in a field of a parameter set and comprised into the dataset header.

6. The method of claim 4, wherein in said first mode can be further represented in two additional different sub-modes:
   a first sub-mode wherein all $AU_i$ of the same class are stored contiguously in the file, and
   a second sub-mode wherein $AU_i$ of the same genomic regions are stored contiguously in the file.

7. The method of claim 6, wherein said indexing table contains the following information:
   a positional information, expressed as number of nucleotides, of the left-most mapped base among all reads or read pairs contained in the Access Unit, with regards to the reference sequence,
   a positional information, expressed as number of nucleotides, of the right-most mapped base among all reads or read pairs contained in the Access Unit, with regards to the reference sequence,
   a list of offsets, expressed as number of bytes, of the first byte of each descriptors data block of each Access Unit, with respect to the first byte of the Dataset payload,
   list of descriptor stream sizes, when said first mode is used, and
   list of Access Unit sizes, when said second mode is used.

8. The method of claim 7, wherein for the case of streaming information, the values of start coordinate $s_i$ and end coordinates $e_i$ of said Access Units $AU_i$ are extracted from the header of each Access Unit $AU_i$.

9. The method of claim 8, wherein said distance of read pairs is expressed as a number of bases or coordinates in a reference system.

10. A method for coding genomic data comprising genomic regions, said genomic data being arranged into entropy coded Access Units $AU_i$ said method comprising the steps of:
    coding values of start coordinate $s_i$ and end coordinate $e_i$ of said Access Units $AU_i$ in an indexing table disjointly coded from said Access Units for the case of storing information in a file, and
    coding a threshold value MaxD in the genomic dataset header of said file, wherein said threshold value MaxD specifies the maximum value that the pairing distance of read pairs can assume, when read pairs are present in said genomic data to be coded, such that said read pairs are coded as single entity or are separately coded.

11. The method of claim 10, wherein said indexing table further contains the mapped classes of Access Units such that at the decoder it is possible to selectively identify the entropy coded Access Units according to the classes of data by employing a vector of pointers, without having to entropy decode said Access Units.

12. The method of claim 11, wherein said $AU_i$ comprise a range information named Access Unit range, said Access Unit range representing the genomic range comprised between the AU start position and the right most genomic record position of all genomic records contained in said AU.

13. The method of claim 12, wherein said AU can be of two different modes:
    a first mode in which blocks of data from different descriptors of the same AU are stored contiguously, and
    a second mode in which data blocks belonging to the same descriptors but belonging to different Access Units are stored in contiguous regions of the file.

14. The method of claim 13, wherein said mode information is coded in a field of a parameter set and comprised into the dataset header.

15. The method of claim 13, wherein in said first mode can be further represented in two additional different sub-modes:
    a first sub-mode wherein all $AU_i$ of the same class are stored contiguously in the file, and
    a second sub-mode wherein Access Units of the same genomic regions are stored contiguously.

16. The method of claim 15, wherein said indexing table contains the following information:
- a positional information, expressed as number of nucleotides, of the left-most mapped base among all reads or read pairs contained in the Access Unit, with regards to the reference sequence,
- a positional information, expressed as number of nucleotides, of the right-most matching base among all reads or read pairs contained in the Access Unit, with regards to the reference sequence,
- a list of offsets, expressed as number of bytes, of the first byte of each descriptor data block of each Access Unit, with respect to the first byte of the Dataset payload,
- list of descriptor stream sizes when said first mode is use, and
- list of access unit sizes when said second mode is used.

17. The method of claim 16, wherein said distance of read pairs is expressed as a number of bases or coordinates in a reference system.

18. A method for decoding compressed coded genomic data comprising genomic regions, said coded genomic data being arranged into entropy coded Access Units $AU_i$ said method comprising the steps of:
- parsing values of start coordinate $s_i$ and end coordinate $e_i$ of said Access Units $AU_i$ from an indexing table disjointly coded from said Access Units for the case of information stored in a file, and
- parsing a threshold value MaxD from the genomic dataset header of said file, wherein said threshold value MaxD specifies the maximum value that the pairing distance of read pairs can assume, when read pairs are present in said genomic encoded data, such that said read pairs are coded as single entity or are separately coded.

19. The method of claim 18, wherein said indexing table further contains the mapped classes of Access Units such that it is possible to selectively identify the entropy coded Access Units according to the classes of data by employing a vector of pointers, without having to entropy decode said Access Units.

20. The method of claim 19, wherein said access units comprise a range information named Access Unit range, said Access Unit range representing the genomic range comprised between the AU start position and the right most genomic record position of all genomic records contained in said AU.

21. The method of claim 20, wherein said AU can be of two different modes:
- a first mode in which blocks of data from different descriptors of the same AU are stored contiguously, and
- a second mode in which data blocks belonging to the same descriptors but belonging to different Access Units are stored in contiguous regions of the file.

22. The method of claim 21, wherein said mode information is parsed from a field of a parameter set and comprised into the dataset header.

23. The method of claim 21, wherein said first mode can be further represented in two additional different sub-modes:
- a first sub-mode wherein all $AU_i$ of the same class are stored contiguously in the file, and
- a second sub-mode wherein Access Units of the same genomic regions are stored contiguously.

24. The method of claim 23, wherein said indexing table contains the following information:
- a positional information, expressed as number of nucleotides, of the left-most mapped base among all reads or read pairs contained in the Access Unit, with regards to the reference sequence,
- a positional information, expressed as number of nucleotides, of the right-most mapped base among all reads or read pairs contained in the Access Unit, with regards to the reference sequence,
- a list of offsets, expressed as number of bytes, of the first byte of each descriptor data block of each Access Unit, with respect to the first byte of the Dataset payload,
- list of descriptor stream sizes when said first mode is used, and
- list of Access Unit sizes when said second mode is used.

25. The method of claim 24, wherein said distance of read pairs is expressed as a number of bases or coordinates in a reference system.

26. A non-transitory computer-readable medium comprising instructions that when executed cause at least one processor to perform the selective access method of claim 1.

27. A non-transitory computer-readable medium comprising instructions that when executed cause at least one processor to perform the coding method of claim 10.

28. A non-transitory computer-readable medium comprising instructions that when executed cause at least one processor to perform the decoding method of claim 18.

* * * * *